United States Patent [19]
Yamazaki et al.

[11] Patent Number: 5,513,640
[45] Date of Patent: May 7, 1996

[54] DIAGNOSTIC ULRASOUND SYSTEM

[75] Inventors: Nobuo Yamazaki; Fumiyasu Sakaguchi, both of Otawara, Japan

[73] Assignee: Kabushiki Kaisha Toshiba, Kanagawa, Japan

[21] Appl. No.: 415,479

[22] Filed: Mar. 31, 1995

[30] Foreign Application Priority Data

Jun. 24, 1994 [JP] Japan ................................. 6-143528
Feb. 9, 1995 [JP] Japan ................................. 7-21795

[51] Int. Cl.$^6$ ..................................................... A61B 8/00
[52] U.S. Cl. ............................. 128/661.09; 128/660.05
[58] Field of Search ..................... 128/660.05, 660.06, 128/660.07, 661.08, 661.09, 661.10, 662.02; 73/861.25

[56] References Cited

U.S. PATENT DOCUMENTS

| | | | |
|---|---|---|---|
| 4,800,891 | 1/1989 | Kim | 128/661.09 |
| 5,170,792 | 12/1992 | Sturgill et al. | 128/661.09 |
| 5,285,788 | 2/1994 | Arenson et al. | |

FOREIGN PATENT DOCUMENTS 6-114059  10/1992  Japan.

OTHER PUBLICATIONS

"Colour Doppler Velocity Imaging of the Myocardium", W. N. McDicken et al., Ultrasound in Med. & Biol., 18(6/7):651–654 (1992).

*Primary Examiner*—George Manuel
*Attorney, Agent, or Firm*—Finnegan, Henderson, Farabow, Garrett & Dunner

[57] ABSTRACT

A diagnostic ultrasound system is provided for displaying a color image of a motion of a tissue scans an ultrasonic pulse signal along a tomographic plane to acquire an electrical echo signal, extracts a Doppler signal from the echo signal, calculates velocity data concerning the motion of the tissue for respective sample points on the tomographic plane on the basis of the Doppler signal, and forms data of a B-mode tomographic image on the basis of the echo signal. The system comprises an element for setting a scale along which each of the velocity data over a measurable band of frequencies of the Doppler signal is assigned to each gradation data for color display, the measurable band of frequencies being limited by a pulse repetition frequency of the ultrasonic pulse signal and a given low-velocity band of the measurable frequency band being enhanced in the gradation data than a remaining velocity band of the measurable band, an element for converting the velocity data into the gradation data according to the scale, an element for blanking either one of the converted gradation data and the calculated velocity data at every sample point when each of them exceeds a specified threshold, and an element for displaying the velocity color image subjected to blanking and superimposed on the B-mode tomographic image.

27 Claims, 24 Drawing Sheets

DIAGNOSTIC ULRASOUND SYSTEM

BACKGROUND OF THE INVENTION

1. Field of the Invention

The present invention relates to a diagnostic ultrasound system, or more particularly, to a diagnostic ultrasound system adaptable to tissue Doppler imaging based on an ultrasonic pulsed-wave Doppler technique.

2. Description of the Related Art

In the past, a diagnostic ultrasound system having a tissue Doppler imaging (TDI) feature has been disclosed, for example, in Japanese Patent Laid-Open No. 6-114059 (of which title of the invention is an "ultrasound color Doppler tomography system") proposed by the present applicant. The diagnostic ultrasound system described in the unexamined patent publication has a feature that uses a pulsed-wave Doppler technique and a lowpass filter to detect the motion velocities of tissues including the cardiac muscle and vascular wall, compute various physical volumes relevant to motion on the basis of the motion velocities, and display the results of computation in appropriate modes in color. For detecting the motion velocity of a tissue, since the motion velocity of a tissue is markedly lower than a blood flow velocity, the pulse repetition frequencies (PRF) of transmitted ultrasonic pulsed waves (rate pulses) are lowered to enable measurement of super-low motion velocities of tissues.

Various modes are available for color display of the results of computation. In the invention described in the unexamined patent publication, two-dimensional color display has been proposed. As for the gradations for the color display, a procedure used for the blood flow imaging, which is implemented in a color Doppler system and shares concepts with tissue Doppler imaging, can be employed.

In the blood flow imaging, a band of Doppler shift frequencies fd ranging from −fr/2 to fr/2 (where, fr denotes a pulse repetition frequency of an ultrasonic pulsed wave) is rendered, as shown in FIG. 27, in 32 gradation (grayscale)levels (fr/32 per level) with different color brightnesses or hues. In other words, a scale whose gradation levels associated with velocities (Doppler shifts) have a constantly progressive change is assigned to the whole band of Doppler shift frequencies ranging from −fr/2 to fr/2, thus defining a color-display gradation between red (yellow) to blue (light blue).

As mentioned above, one of the characteristics of tissue Doppler imaging lies in that pulse repetition frequencies (lower frame rates) of ultrasonic waves are set to lower values in order to enable measurement of ultra-low motion velocities of tissues. Owing to the characteristic of enabling measurement of an ultra-low motion velocity, the band of Doppler shift frequencies required for display images produced by tissue Doppler imaging is narrower than that required for display images produced by blood flow imaging of ranges, for example, from −fr/8 to fr/8.

Nevertheless, at present, the assignment of a color-display gradation adopted for blood flow imaging cannot help applying to tissue Doppler imaging as it is. As a result, the number of gradation levels assigned to a low-velocity band is quite limited. A tissue region to be observed; such as, the cardiac muscle appears, for example, in red of almost the same hue or brightness. It is therefore very hard to visually assess a difference in velocity in a low-velocity band image. Even if a difference in velocity smaller than fr/32 can be detected, since a displayed hue or brightness is unchanged, high-precision detectability is canceled out by poor displaying ability. There still exists an unsolved problem that the high-precision detectability cannot be exerted fully.

When tissue Doppler imaging is used for diagnosis, it should be discerned promptly whether the cardiac muscle or any other tissue region of interest is normal or abnormal. Using the conventional display technique, the levels of a color-display gradation are assigned uniformly between a low-velocity band and a high-velocity band. The displaying ability for the low-velocity band is, as described previously, poor. There is therefore difficulty in discerning whether a diagnostic region is normal or abnormal. Consequently, it takes too much time for diagnosis. Moreover, an examining physician is requested to have high expertise.

SUMMARY OF THE INVENTION

The present invention attempts to solve the aforesaid unsolved problems. The first object of the present invention is to improve the ability to display a low-velocity band image by making the most of the function relevant to measurements of motion concerning a low-velocity band which is available in tissue Doppler imaging.

The second object of the present invention is to achieve the first object and provide images that are produced by tissue Doppler imaging (hereinafter, TDI images) and facilitate easy discernment of whether a region of interest (hereinafter, ROI)is normal or abnormal.

For achieving the above objects, as one aspect of the invention, there is provided a diagnostic ultrasound system for displaying a color image of a motion of a tissue contained on a subject's tomographic plane, comprising: an element for scanning an ultrasonic pulse signal along the tomographic plane so as to acquire an electrical echo signal corresponding to an ultrasonic signal reflected from the tomographic plane; an element for extracting a Doppler signal from the echo signal, the Doppler signal being Doppler-shifted by the motion of the tissue; an element for calculating velocity data concerning the motion of the tissue for respective sample points on the tomographic plane on the basis of the Doppler signal; an element for setting a scale along which each of the velocity data over a measurable band of frequencies of the Doppler signal is assigned to each gradation data for color display, the measurable band of frequencies being limited by a pulse repetition frequency of the ultrasonic pulse signal and a given low-velocity band of the measurable frequency band being enhanced in the gradation data than a remaining velocity band of the measurable band; an element for converting the velocity data into the gradation data according to the scale; and an element for displaying the color image using the gradation data provided by the velocity converting element.

Preferably, the extracting element comprises a low-pass filter for selectively extracting the Doppler signal. Still preferably, the scale is non-linear in a ratio between changes in the velocity data and changes in the gradation data. For example, the ratio in the given low-velocity band is higher than said ratio in the remaining velocity band. For example, the specified low-velocity band is any of $-fr/8 \leq fd \leq fr/8$, $-fr/12 \leq fd \leq fr/12$, and $-fr/16 \leq fd \leq fr/16$, where fr represents the pulse repetition frequency of the ultrasonic pulse signal and fd represents a Doppler shift frequency. It is preferred that at least maximum data of the color code data is discontinuous in gradation levels from a series of remaining data of the color code data.

A diagnostic ultrasound system in accordance with the above aspect of the present invention is adaptable to tissue Doppler imaging. For this imaging technique, the cardiac muscle or any other region is scanned according to an ultrasonic pulsed-wave Doppler method. Echoes are then obtained, whereby a motion velocity is computed for each of sample points on a scanned tomographic plane. The motion velocity is visualized in two-dimensional color display mode. For the display, the slope of a scale of velocity data versus color-display gradation data to be assigned to a low-velocity band (for example, $-fr/8 \leq fd \leq fr/8$) within a velocity range measurable by the ultrasonic pulsed-wave Doppler that is equivalent to a band of Doppler shifts; $-fr/2 \leq fd \leq fr/2$ (where fr denotes a pulse repetition frequency of an ultrasonic pulsed wave, and fd denotes a Doppler shift) is larger than that of the other velocity band. This results in an increase in display resolution for the low-velocity band. A minute change in low-velocity motion of the cardiac muscle is therefore visualized with high sensitivity as a change in multi-level gradation of color brightness degrees (luminances) or hues. Consequently, even if an attempt is made to upgrade the function relevant to measurements of low-velocity motion by specifying lower pulse repetition frequencies, the function will not be impaired. Moreover, a pixel rendering a velocity comparable to a maximum gradation level is displayed with such a hue as making the pixel discontinuous with the other pixels rendering lower velocities. The pixel rendering the velocity comparable to a maximum gradation level is therefore readily discernible. Thus, discernible efficiency improves.

As another aspect of the invention is provided by a diagnostic ultrasound system for displaying a color image of a motion of a tissue contained on a subject's tomographic plane, the color image being superposed on a B-mode tomographic image of the subject's tomographic plane, the system comprising: an element for scanning an ultrasonic pulse signal along the tomographic plane to acquire an electrical echo signal corresponding to a reflected ultrasonic signal from the tomographic plane; an element for extracting a Doppler signal from the echo signal, the Doppler signal being Doppler-shifted by the motion of the tissue; an element for calculating velocity data concerning the motion of the tissue for respective sample points on the tomographic plane on the basis of the Doppler signal; an element for forming data of the B-mode tomographic image on the basis of the echo signal; an element for blanking the velocity data at every sample point when each of the velocity data exceeds a specified threshold; and an element for displaying the color image by coloring the velocity data and by superimposing the velocity data subjected to blanking by the blanking element on the data of the B-mode tomographic image.

Still another aspect of the invention is provided by a diagnostic ultrasound system for displaying a color image of a motion of a tissue contained on a subject's tomographic plane, the color image being superposed on a B-mode tomographic image of the subject's tomographic plane, the system comprising: an element for scanning an ultrasonic pulse signal along the tomographic plane to acquire an electrical echo signal corresponding to a reflected ultrasonic signal from the tomographic plane; an element for extracting a Doppler signal from the echo signal, the Doppler signal being Doppler-shifted by the motion of the tissue; an element for calculating velocity data concerning the motion of the tissue for respective sample points on the tomographic plane on the basis of the Doppler signal; an element for forming data of the B-mode tomographic image on the basis of the echo signal; an element for setting a scale along which each of the velocity data over a measurable band of frequencies of the Doppler signal is assigned to each gradation data for color display, said measurable band of frequencies being limited by a pulse repetition frequency of the ultrasonic pulse signal and a given low-velocity band of the measurable frequency band being enhanced in the gradation data than a remaining velocity band of the measurable band; an element for converting the velocity data into the gradation data according to the scale; an element for blanking either one of the converted gradation data and the calculated velocity data at every sample point when each of either one exceeds a specified threshold; and an element for displaying the color image by coloring the velocity data and by superimposing the velocity data subjected to blanking by the blanking element on the data of the B-mode tomographic image.

Preferably, the scale setting element is an element that sets the scale in which a ratio of changes in the gradation data to changes in the Doppler frequency is higher than a corresponding ratio for analysis of fluid motion within the subject and the velocity data larger than a reference velocity data corresponding to maximums of the gradation data are all assigned to the maximums. It is preferred that the diagnostic ultrasound system further comprises an element for setting the threshold independently of the scale. It is also preferred that the scale setting element is an element that automatically sets the threshold in connection with setting the scale.

In consequence, in the same way as explained above, an increase in display resolution for the low-velocity band is provided. In addition, sample points having velocities higher than the specified threshold on the tomographic plane dose not display the tissue Doppler image and, instead of it, display only the B-mode tomographic image as the background image hidden behind the tissue Doppler image. Properly specifying the threshold enables to exclude or minimize the meaningless (gradation-less) velocity color region of a tissue.

DETAILED DESCRIPTION OF THE PREFERRED EMBODIMENTS

First Embodiment

The first embodiment of the present invention will be described in conjunction with FIGS. 1 to 6. A diagnostic ultrasound system in accordance with the first embodiment is a diagnostic system for producing TDI images of the cardiac muscle (cardiac wall) that is a tissue.

Figure 1:
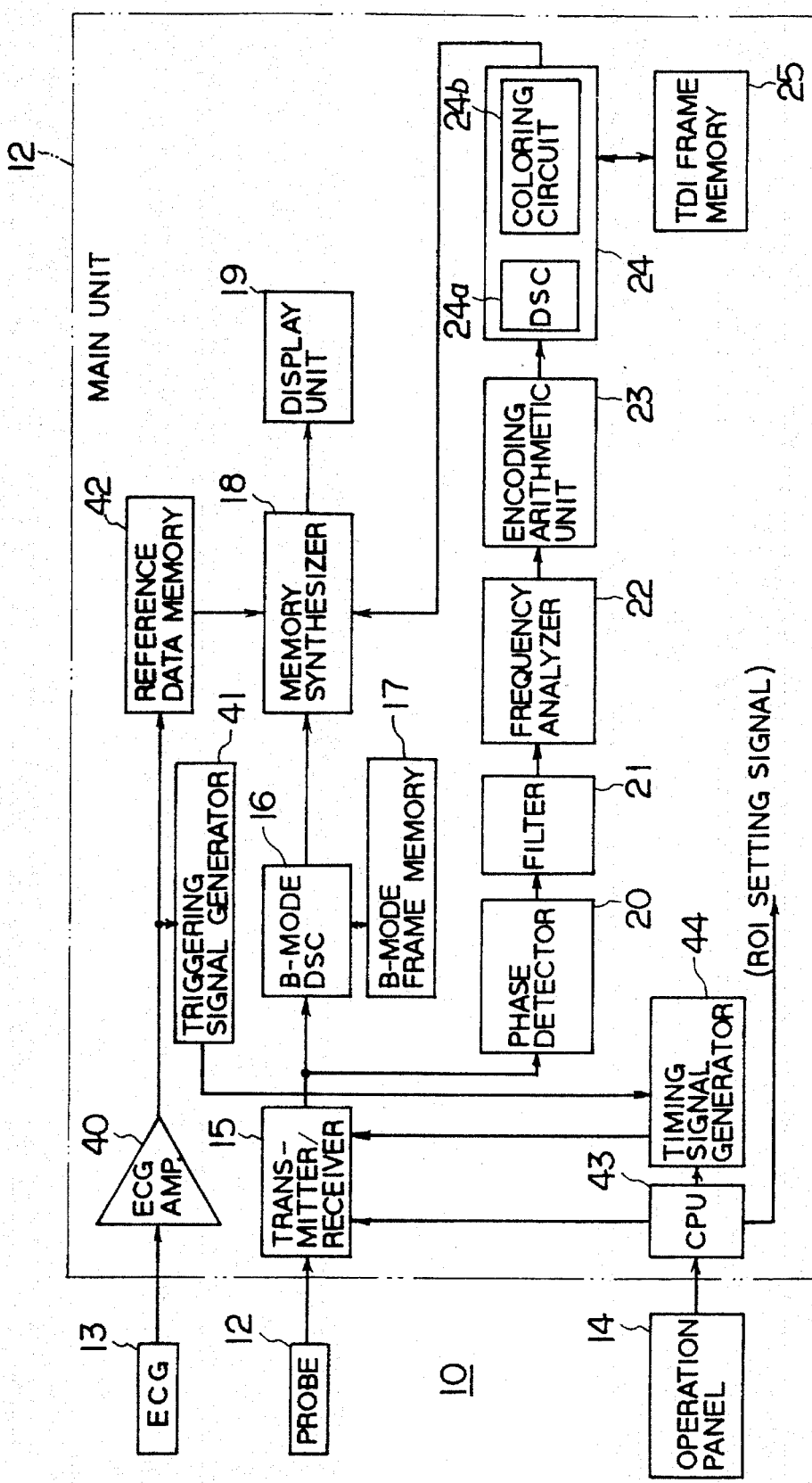
FIG. 1 is a block diagram showing a diagnostic ultrasound system in accordance with the first embodiment of the present invention.

FIG. 1 is a block diagram showing a diagnostic ultrasound system. As illustrated, a diagnostic ultrasound system 10 comprises an ultrasound probe 11 responsible for receiving or transmitting ultrasonic waves from or to a subject, a main unit 12 for driving the ultrasound probe 11 and processing signals received by the ultrasound probe 11, an electrocardiograph (hereinafter, ECG) 13 connected to the main unit 12 in order to detect electrocardiographic information, and an operation panel 14 connected to the main unit 12 and capable of supplying instruction information entered by an operator to the main unit, The main unit 12 is broadly divided into an ultrasound probe system, an ECG system, and an operation panel system according to the type of signal line concerned, The ultrasound probe system has an ultrasonic-wave transmitter/receiver 15 connected to the ultrasound probe 11 and includes a B-mode digital scan converter (hereinafter, B-mode DSC) 16, a B-mode frame memory 17, a memory synthesizer 18, and a display unit 19 which are installed in the output stage of the ultrasonic-wave transmitter/receiver 15. The ultrasound probe system further includes a phase detector 20 for use in color mapping, a filter 21, a frequency analyzer 22, an encoding arithmetic unit 23, a tissue Doppler imaging DSC (hereinafter, TDI DSC) 24, and a tissue Doppler imaging frame memory (hereinafter, TDI frame memory) 25, all of which are connected to the ultrasound probe 11. The ECG system has an ECG amplifier 40 connected to the ECG 13 and includes a triggering signal generator 41 and a reference data memory 42 which are connected in the output stage of the amplifier 40. The operation panel system includes a CPU 43 that inputs operation information entered at the operation panel 14, and a timing signal generator 44 working under the control of the CPU 43. The CPU 43 can supply a ROI setting signal representing a command entered at the operation panel 14 by an operator to component elements required for setting a ROI.

In this embodiment, the ultrasound probe 11 and ultrasonic-wave transmitter/receiver 15 constitute a scanning means in accordance with the present invention. The phase detector 20 serves as a sampling means. The filter 21 and frequency analyzer 22 constitute a velocity arithmetic means in accordance with the present invention. The TDI DSC 24, TDI frame memory 25, memory synthesizer 18, and display unit 19 constitute a display means in accordance with the present invention. The encoding arithmetic unit 23 has the capabilities of a scale setting means and a velocity converting means.

A phased-array transducer in which a plurality of strip-shaped piezoelectric oscillators are set in array is incorporated in the ultrasound probe 11. The piezoelectric oscillators are energized in response to drive signals sent from the ultrasonic-wave transmitter/receiver 15. By controlling the delay times of drive signals, scan directions can be changed to enable electronic sector scanning. Delay-time patterns set for the ultrasonic-wave transmitter/receiver 15 are controlled by the CPU 43 using a reference signal sent from the timing signal generator 44, as a representation of a reference time instant. The ultrasonic-wave transmitter/receiver 15 supplies drive voltages, which are generated according to the delay-time patterns controlled dependently on scan directions, to the ultrasound probe 11. When receiving the drive voltages, the ultrasound probe 11 allows the transducer to transform the voltages into ultrasonic waves. The resultant ultrasonic waves are transmitted to the heart of a subject. The transmitted ultrasonic waves are reflected from tissues including the heart and returned to the ultrasound probe 11. The transducer in the probe 11 then transforms the reflected ultrasonic waves into voltages (echoes). The echoes are supplied to the ultrasonic-wave transmitter/receiver 15.

A signal processor in the ultrasonic-wave transmitter/receiver 15 beam-forms the input echoes by delaying the echoes in the same manner as it does for transmission, and produces an echo beam that is equivalent to an ultrasound beam focused in the scan direction. The echo beam resulting from beam forming is subjected to phase detection and then supplied to the B-mode DSC 16. The DSC 16 converts echo data resulting from ultrasound scanning into standard TV data and supplies the standard TV data into the memory synthesizer 18. Concurrently, the B-mode DSC 16 places data of a plurality of images produced in any cardiac phase in the B-mode frame memory 17.

The echoes processed by the ultrasonic-wave transmitter/receiver 15 are also supplied to the phase detector 20. The phase detector 20 includes mixers and low-pass filters. Echoes reflected from a region making motion; such as, the cardiac muscle have undergone a Doppler shift due to the Doppler effect. The phase detector 20 performs phase detection on the echoes to discriminate frequencies of Doppler signals and then supplies Doppler signals alone to the filter 21.

Figure 2:
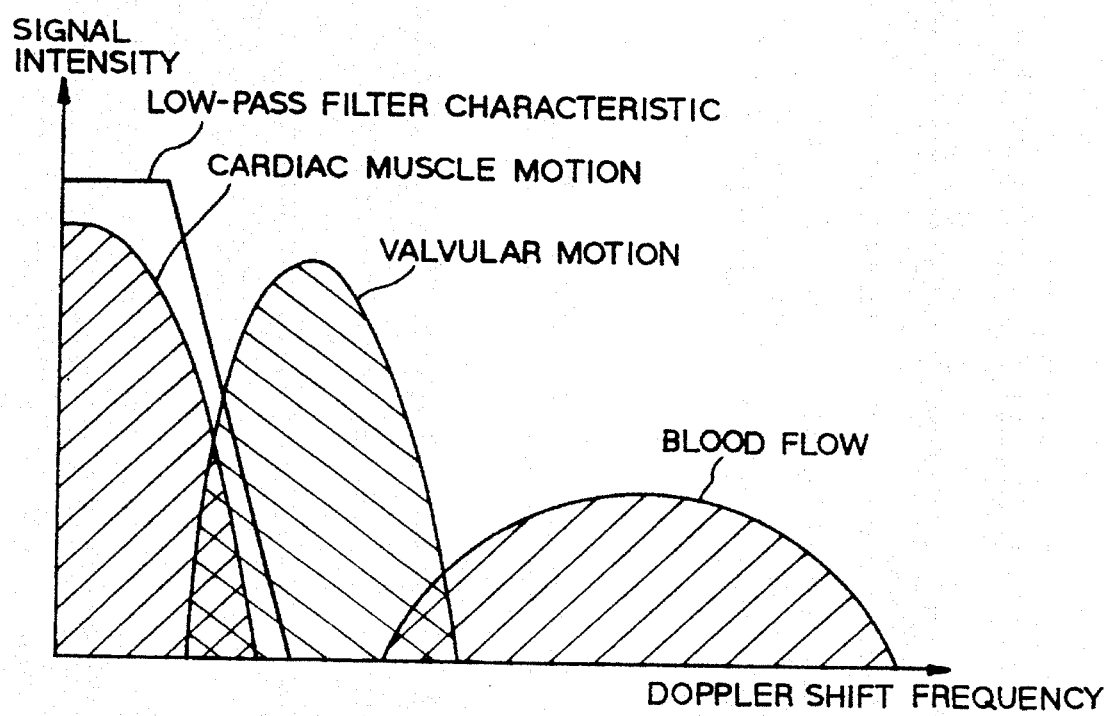
FIG. 2 is a graph expressing characteristics of Doppler shift frequencies (motion velocity) induced by tissues or blood flow and a characteristic of a low-pass filter employed in tissue Doppler imaging according to the first embodiment.

The filter 21 removes unnecessary signal components; such as, valvular motion signal components returned from any region other than the cardiac wall or blood flow signal components from the Doppler signals resulting from phase detection on the basis of the relationship of the magnitudes of motion velocities; the magnitude of a motion velocity of the cardiac muscle<that of a valve<that of blood flow (See FIG. 2). The filter 21 thus highly efficiently detects the Doppler signals returned from the cardiac muscle and related to the direction of an ultrasound beam. In this case, the filter 21 plays the role of a low-pass filter.

The filter is included in even a color Doppler tomography system that has already been put to practical use and designed for acquiring blood flow information. For the color Doppler tomography system for acquiring blood flow information, the filter serves as a high-pass filter for handling echoes containing a mixture of blood flow, cardiac wall, and valvular motion of Doppler signals, and thus eliminates the Doppler signals other than the blood flow Doppler signals. If the filter is designed to serve as either of low-pass and high-pass filters according to a purpose of use, it can enjoy the general-purpose characteristic.

The Doppler signals filtered by the filter 21 are supplied to the frequency analyzer 22 lying in the subsequent stage. The frequency analyzer 22 adopts fast Fourier transform (hereinafter, FFT) or autocorrelation that is a technique of frequency analysis employed in blood flow measurements based on an ultrasonic-wave Doppler technique, wherein average velocities or maximum velocities to be detected within an observation time interval (time window) at sample points on a tomographic plane to be scanned are computed. To be more specific, for example, the FFT or autocorrelation technique is used to compute average frequencies of Doppler signals at individual sample points (that is, average motion velocities to be observed at the sample points) and variances (spectral incoherences of Doppler signals). Furthermore, the FFT technique is used to compute maximum frequencies of the Doppler signals (that is, maximum motion velocities to be observed at the sample points) substantially in real time. The results of analysis on the frequencies of the Doppler signals are supplied as color Doppler information concerning motion velocities to the encoding arithmetic unit 23 in the subsequent stage.

The encoding arithmetic unit 23 has the capability of a CPU, and encodes Doppler shift frequencies fd, which are induced at the sample points on the tomographic plane and provided by the frequency analyzer 22, into velocity data composed of a given number of bits using a designated velocity conversion scale. According to the ultrasonic pulsed-wave Doppler technique, pulse repetition frequencies fr of ultrasonic pulsed waves correspond to sampling rates. Based on the sampling theorem, a maximum measurable Doppler shift frequency fdmax is determined according to the following formula:

$$fd=fr/2$$

A Doppler shift frequency fd that can be computed by the frequency analyzer 22 and does not trigger aliasing has the following band:

$$-fr/2 \leq fd \leq fr/2$$

Within the Doppler shift frequency (velocity) band, a band expressed below is quantized at a quantization factor of fr/128, and thus encoded into velocity codes each having a data length of, for example, 5 bits.

$$-fr/8 \leq fd \leq fr/8$$

In this case, when the Doppler shift frequency fd ranges as follows:

$$-fr/2 \leq fd \leq -fr/8$$

it is associated with an encoded data obtained when the fd has a value −fr/8 comparable to a maximum gradation level for one motion direction (for example, for a direction of receding from an ultrasound beam). When the Doppler shift frequency fd ranges as follows:

$$fr/8 < fd \leq fr/2$$

it is associated with an encoded data obtained when the fd has a value fr/8 comparable to a maximum gradation level for the other motion direction (for example, for a direction of approaching an ultrasound beam).

Figure 3:
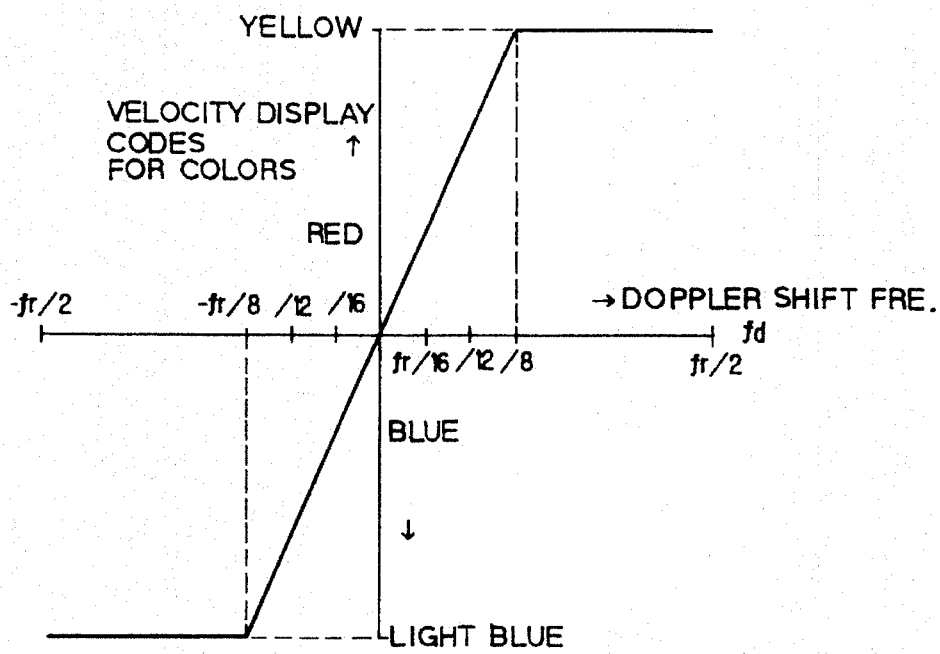
FIG. 3 is a graph expressing an example of a velocity conversion scale according to the first embodiment.
Figure 4:
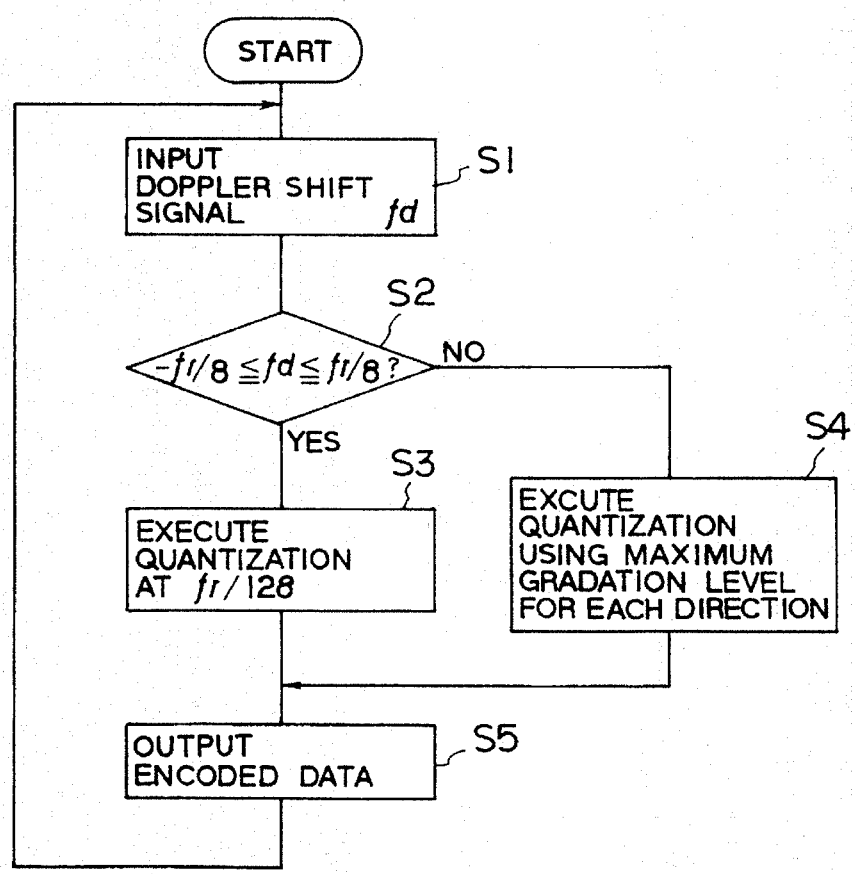
FIG. 4 is a brief flowchart describing a sequence executed by an encoding arithmetic unit in the first embodiment.

As a result, a velocity conversion scale whose abscissae cover a Doppler shift frequency band of $-fr/2 \leq fd \leq fr/2$ and whose ordinates indicate velocity codes expressed with changing hues of color-display colors; red (yellow) and blue (light blue) appears as shown in FIG. 3. That is to say, when the absolute value of a velocity exceeds a quotient of fr/8, the colors are saturated. Velocity display data of 5 bits long that is obtained for each sample point and has undergone encoding is supplied to the TDI DSC 24 in the subsequent stage. The aforesaid procedure corresponds to steps S1 to S5 in FIG. 4.

The TDI DSC 24 includes a DSC circuit 24a for changing scanning forms and a coloring circuit 24b having a look-up table for use in converting encoded velocity display data into color data. Velocity display data sent from the encoding arithmetic unit 23 are converted into standard TV signals by the DSC circuit 24a, and further converted into color data by the coloring circuit 24b. The converted signals are supplied to the memory synthesizer 18.

Figure 5:
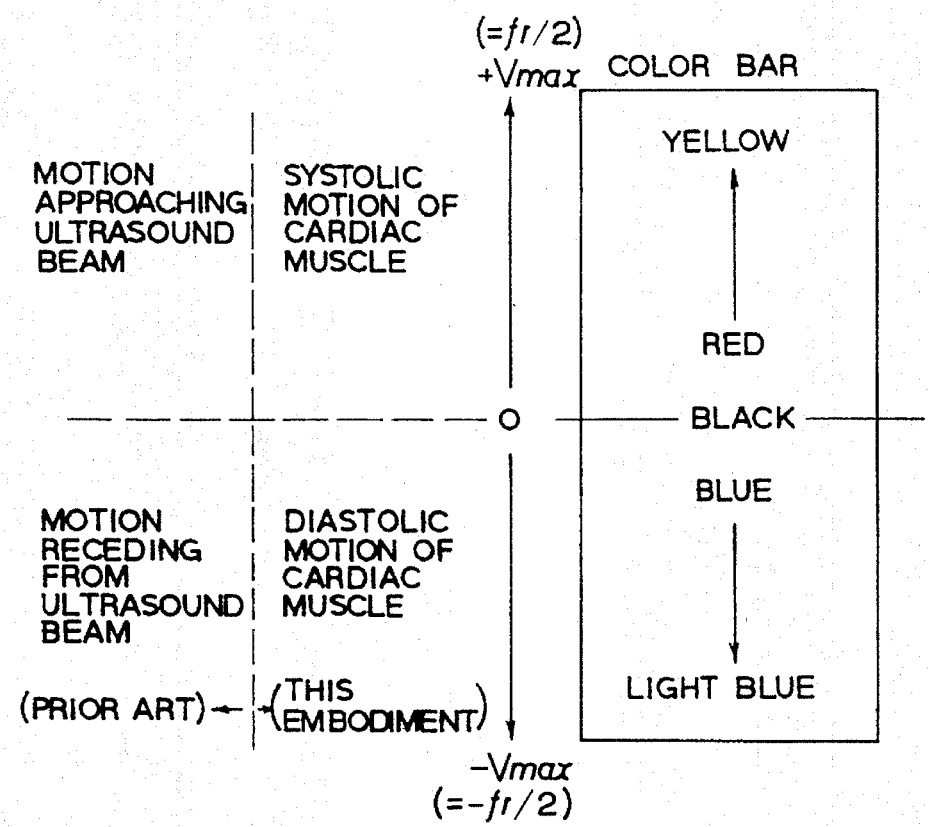
FIG. 5 shows a relationship between the motion direction of the cardiac muscle and a color bar in the first embodiment.

Now, mention will be made of a color display form used to render a velocity of the cardiac muscle and employed in the coloring circuit 24b. The color display form is broadly classified into (i) a form of displaying magnitudes (absolute values) of velocities, (ii) a form of displaying motion directions and magnitudes of velocities, and (iii) a form of displaying motion directions. The display form (i) falls into form (a) in which display is monochrome and brightnesses are dependent on magnitudes and form (b) in which colors are dependent on magnitudes. The display form (ii) includes a form in which directions are discriminated with hues and magnitudes are indicated with their brightnesses, and a form in which directions are indicated with hues and magnitudes are indicated with changes in their hues. Herein, an adaptable form of rendering velocities is limited dependently on a velocity information structure. The coloring circuit 24b in the TDI DSC 24 determines colors as shown in FIG. 5. Specifically, according to a conventional method of rendering a motion approaching an ultrasound beam in red and a motion receding from the ultrasound beam in blue, the systolic motion of the cardiac muscle is rendered in red (yellow) and the diastolic motion thereof is rendered in blue (light blue). With a larger absolute value, red or blue is gradated into yellow or light blue. As a result, velocity display data concerning a desired low-velocity band of $-fr/8 \leq fd \leq fr/8$ is converted into color information of 32 gradation levels, which represent a series of color-display colors from light blue through blue and red to yellow, for each motion direction.

The DSC circuit 24a places a plurality of color Doppler images produced in any cardiac phase in the TDI frame memory 25.

The aforesaid ECG 13 detects electrocardiographic information of a subject in respective cardiac phases of the subject. The detected signal is supplied to each of the triggering signal generator 41 and reference data memory 42 via the ECG amplifier 40. The reference data memory 42 stores electrocardiographic information acquired in the respective cardiac phases and supplies required information to the memory synthesizer 18 when it becomes necessary. The triggering signal generator 41 informs the timing signal generator 44 of timing information concerning the cardiac phases. The timing signal generator 44 operates under the control of the CPU 43 that controls delay-time patterns to be set for the ultrasonic-wave transmitter/receiver 15 in response to an instruction entered at the operation panel 14. When notified of the timing of each cardiac phases by the triggering signal generator 41, the timing signal generator 44 outputs a reference signal for use in transmitting or receiving ultrasonic waves to or from the ultrasonic-wave transmitter/receiver 15.

As mentioned above, a B-mode image signal sent from the B-mode DSC 16, a TDI-mode image signal sent from the TDI DSC 24, and, if necessary, electrocardiographic information supplied from the reference data memory 42 are fed to the memory synthesizer 18. The memory synthesizer 18 superposes these input signals. Data resulting from the superposition is supplied to the display unit 19. The display unit 19 includes a cathode-ray tube (hereinafter, CRT).

Figure 6:
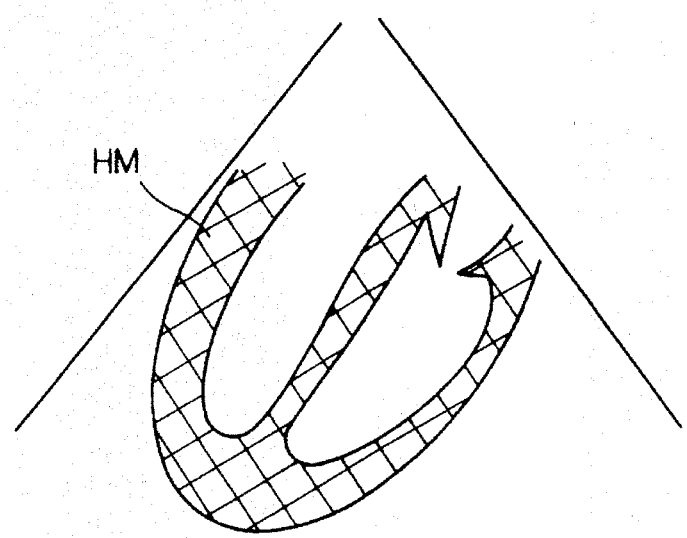
FIG. 6 shows an example of display of the cardiac muscle in the first embodiment.

As a result, since the blood flow Doppler signal and valvular Doppler signal have already been cut off by the filter 21, a tomographic image, in which a B-mode tomographic image (black-and-white gradation) of the heart and a color image rendering the motion of the cardiac muscle with colors contained in a color bar shown in FIG. 5 according to the velocity conversion scale shown in FIG. 3 are superposed on each other, is, as shown in FIG. 6, displayed substantially in real time on the display unit 19 (in FIG. 6, a hatched area indicates the cardiac muscle HM). In other words, the cardiac muscle HM in FIG. 6 appears in red (yellow) during systole and in blue (light blue) during diastole. The colors of red and blue reappear cyclically and in real time. A change in motion velocity during systole or aliastole is expressed substantially in real time as a change in hue of red or yellow, or blue or light blue. The motion velocity of the cardiac muscle HM can be rendered in color substantially in real time and highly accurately. Thus, basic images for use in assessing cardiac hypofunction quantitatively and highly accurately are made available.

In particular, as far as tissue Doppler imaging is concerned, since a super-low-velocity band of $-fr/8 \leq fd \leq fr/8$ is rendered with hues equivalent to 32 gradation levels (quantization rate of 5 bits), which are all of the gradation levels provided by the color bar, for each motion direction, as very small a Doppler shift frequency(that indicates a motion velocity) as a quotient of fr/128 is assigned each gradation level in practice. Compared with the aforesaid conventional method in which all the 32 gradation levels are assigned to the full band of $-fr/2 \leq fd \leq fr/2$, the display ability to render the super-low-velocity band of $-fr/8 \leq fd \leq fr/8$ is upgraded fourfold. This enables the velocity of super-low-velocity motion of the cardiac muscle detected with low pulse repetition frequencies to be rendered in an unprecedentedly large number of gradation levels. A minute difference in velocity concerning a super-low-velocity band is rendered with a display color of a different hue. Consequently, a difference in velocity becomes readily discernible for evaluation.

In clinical assessment conducted by the present applicant, any value ranging from 4 cm/s to 10 cm/s was specified as a maximum velocity for the low-velocity band, and a velocity exceeding the maximum velocity was rendered with a saturated color and encoded into velocity data associated with red or blue of the highest brightness (a change in brightness of a designated color was adopted as color-display gradation data instead of a change in hue). A velocity that triggers aliasing and is calculated on the basis of a sampling rate was four times or eight times higher than the maximum velocity rendered with a saturated color; that is, ranged from 30 cm/s to 40 cm/s. Under this condition, the motion velocity of the ventricle wall was measured. It was confirmed that no aliasing occurred.

Even ultrasonic pulsed waves having the same pulse repetition frequencies as those adopted conventionally are used for scanning, the capacity for measuring the velocity of super-low-velocity motion of a tissue will not be impaired but a high-performance system can be materialized.

Since the diagnostic system in the aforesaid embodiment includes two kinds of frame memories 17 and 25 dedicated to B and TDI modes respectively, if necessary, the diagnostic system may perform cine loop reproduction such as slow-motion reproduction or frame-by-frame reproduction, animated reproduction, or independent or parallel display of images produced in different cardiac phases between B and CFM modes.

The aforesaid tomography system may be provided with a Doppler filter or FFT frequency analyzer for use in rendering the motion of the cardiac muscle on the basis of Doppler principle.

Furthermore, in the aforesaid embodiment, an image on which a TDI image of the cardiac muscle is superposed is a B-mode tomographic image, and a region to be diagnosed is the heart. The present invention is not necessarily limited to this application. For example, the B-mode image may be replaced with an M-mode image (in this case, the component elements required for producing B-mode images are replaced with those required for producing M-mode images). The vascular wall may be diagnosed on behalf of the cardiac muscle (in this case, the cutoff frequency of the filter 21 is set to a value optimal for the vascular wall). Moreover, the B-mode images or M-mode images may not be superposed on a TDI image, but a TDI (color Doppler) image alone may be displayed.

Furthermore, biomedical signals including electrocardiograms may be displayed concurrently or a time lag relative to the R wave of an electrocardiographic signal may be displayed for reference. This display mode is employed in a normal B-mode tomography system or blood flow (color flow) mapping, and helpful for clearly indicating the association of biomedical signals with produced images.

An absolute velocity arithmetic unit may be interposed between the frequency analyzer 22 and encoding arithmetic unit 23 in the aforesaid embodiment. Absolute motion velocities of tissues including the cardiac muscle (that is, velocities in motion directions of tissues at sample points) may be computed by inference, and displayed two-dimensionally in color.

Figure 7:
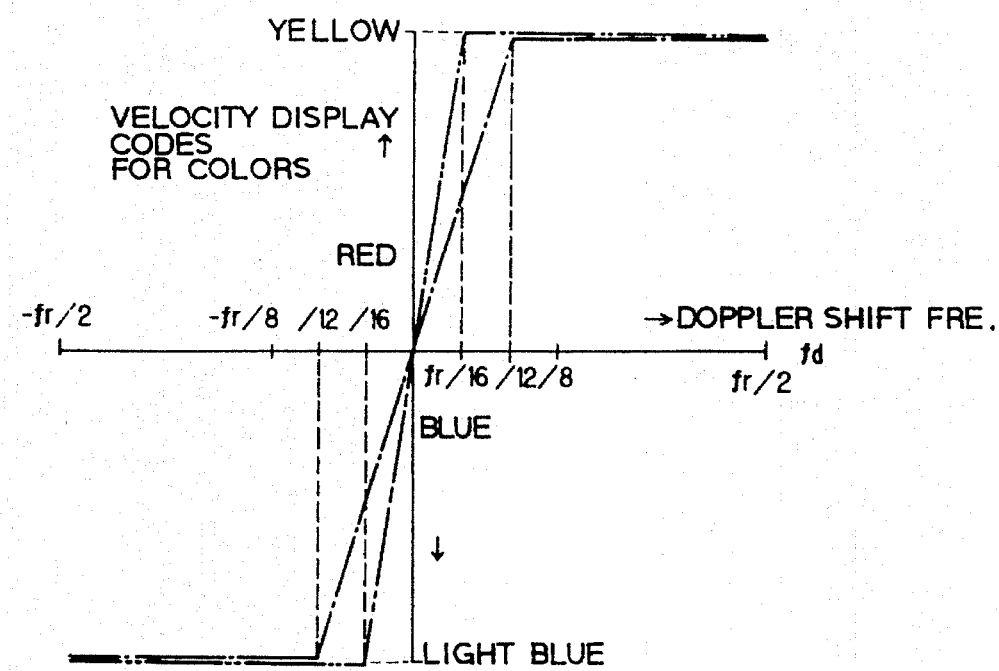
FIG. 7 shows another example of a velocity conversion scale.

On the other hand, the low-velocity band to be rendered in fine gradation levels owing to the superb gradation rendering ability in accordance with the present invention is not limited to the band in the aforesaid embodiment; $-fr/8 \leq fd \leq fr/8$. When the encoding arithmetic unit is programmed differently, a band of $-fr/12 \leq fd \leq fr/12$ plotted as a velocity conversion scale indicated with a dot-dash line in FIG. 7 or a band of $-fr/16 \leq fd \leq fr/16$ plotted as a velocity conversion scale indicated with an alternate long-and-two short-dashes line will do. Any of these frequency bands; $-fr/8 \leq fd \leq fr/8$, $-fr/12 \leq fd \leq fr/12$, and $-fr/16 \leq fd \leq fr/16$ may be selected according to a manual operation signal entered by an operator, so that the operator can designate an appropriate band while viewing a screen on the display unit. For this purpose, the CPU 43 in FIG. 1 should send a selection signal concerning manual operation to the encoding arithmetic unit 23 in response to the manual operation signal propagating from the operation panel 14.

Figure 8:
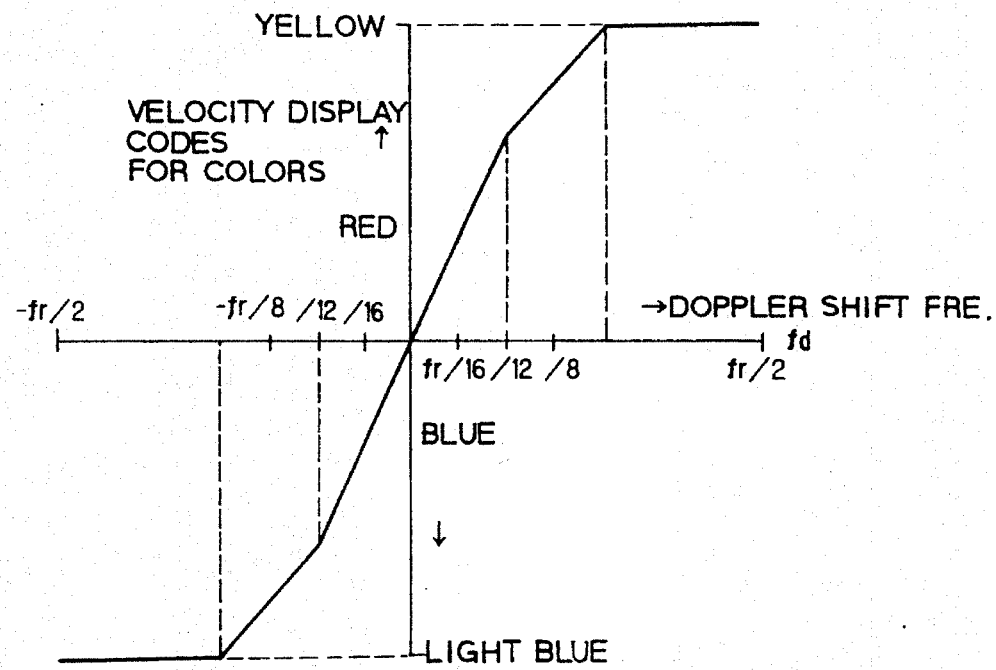
FIG. 8 shows yet another example of a velocity conversion scale.

For enhancement of a low-velocity band in accordance with the present invention, as shown in FIG. 8, a velocity conversion scale having a sharp slope may be assigned to a desired low-velocity band of, for example, $-fr/12 \leq fd \leq fr/12$, and a velocity conversion scale having a moderate slope may be assigned to a middle-velocity band outside the low-velocity band. In this case, an encoding arithmetic unit is used to control transition between adjoining ones of a plurality of slopes of a velocity conversion scale. Consequently, two-dimensional color images reflecting a relationship in velocity between a low-velocity band and a surrounding band can be produced.

Figure 9:
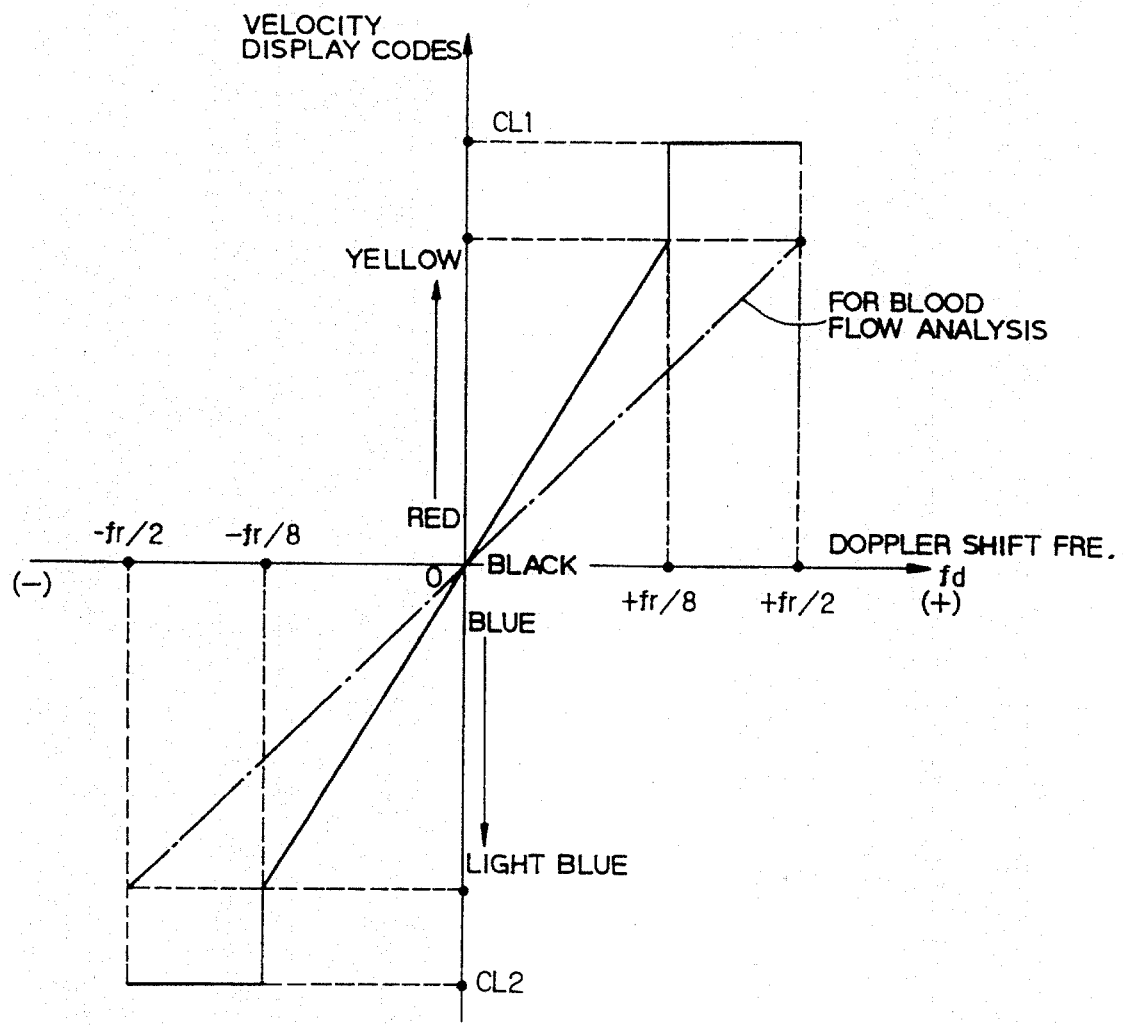
FIG. 9 shows still another example of a velocity conversion scale.
Figure 10:
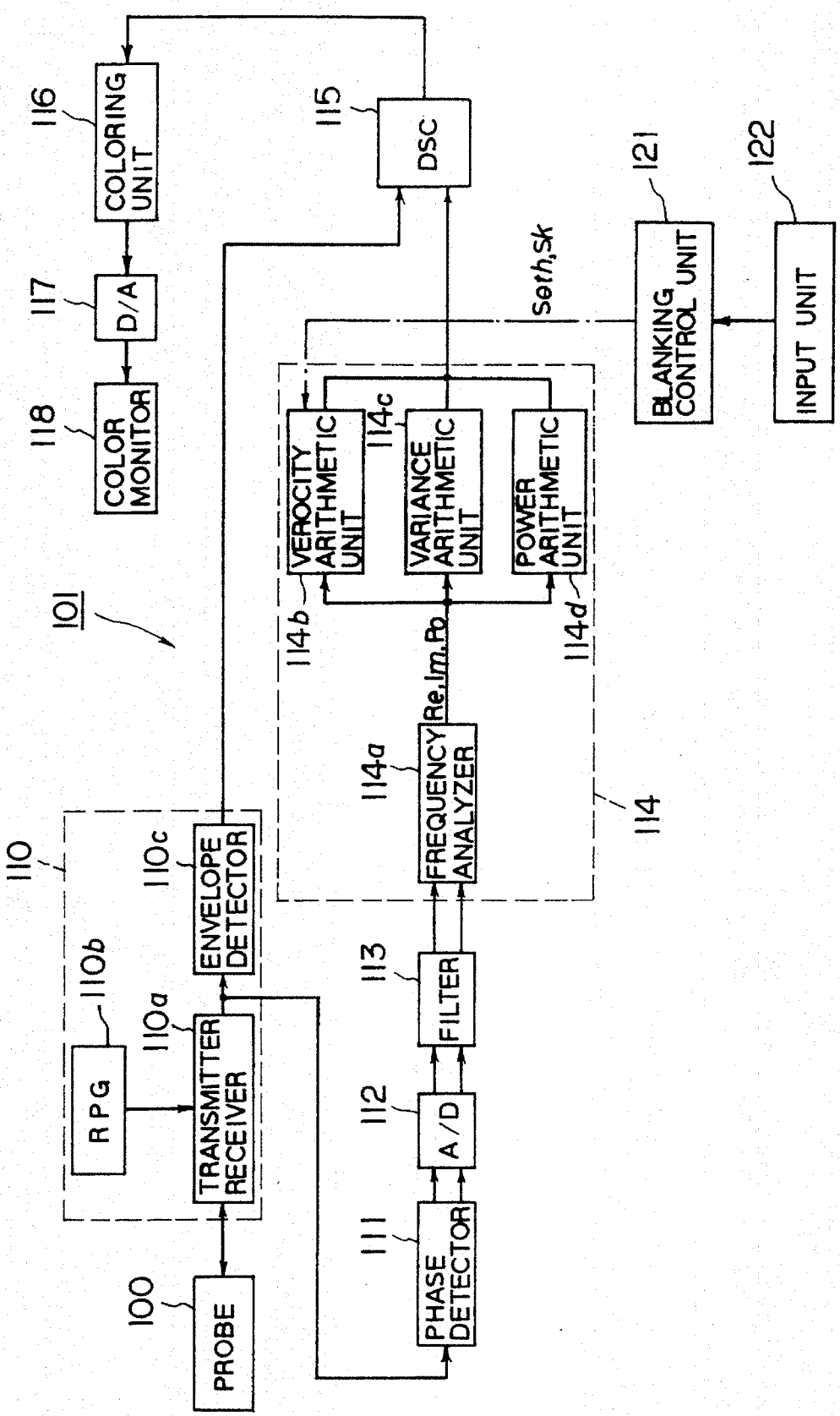
FIG. 10 is a block diagram showing a diagnostic ultrasound system in accordance with the second embodiment of the present invention.

For enhancement of a low-velocity band in accordance with the present invention, a velocity conversion scale indicated with a solid line in FIG. 9 may be employed (a dot-dash line in FIG. 9 indicates a conventional scale dedicated to blood flow analysis). The velocity conversion scale is pre-set as, for example, a storage table in the encoding arithmetic unit 23. Assigned to, for example, a band of $-fr/8 < fd < +fr/8$ defined as a low-velocity band are velocity codes equivalent to gradation levels representing hues that have a progressive (or continuous) change from red to yellow and from blue to light blue for each direction of tissue motion. However, when an averaged Doppler shift frequency fd (that is an average velocity of tissue motion) meets the condition of $fd \geq \pm fr/8$, velocity display codes associated with special colors CL1 and CL2 whose hues are not continuous at all are assigned uniformly to the above low-velocity band but the velocity display codes associated with the hues having a continuous change from red to yellow and from blue to light blue are not. The special colors CL1 and CL2 are produced by mixing a red hue and a blue hue with a certain hue. Needless to say, the velocity thresholds are not limited to $\pm fr/8$ but may be any values that can be modified. The motion velocities of tissues exceeding those defined with a predetermined low-velocity band are discernible at sight owing discontinuous hues. With the enhancement of a low-velocity band, interpretation of diagnostic images gets further easier.

Gradation levels equivalent to velocity display codes necessary for color display in accordance with the present invention may be hues dependent on magnitudes of velocities or brightnesses of red (or blue) dependent on magnitudes of velocities as mentioned above.

The aforesaid embodiment or any variant thereof can be incorporated into a conventional diagnostic ultrasound system capable of performing blood flow Doppler imaging, if necessary.

Second Embodiment

Next, the second embodiment of the present invention will be described in conjunction with FIGS. 10 to 15. The aforesaid first embodiment aims at improving the ability to render a low-velocity band. A diagnostic ultrasound system of the second embodiment attempts not only to improve the rendering ability but also to permit easy diagnosis of discerning whether a ROI is normal or abnormal. For achieving this object, the diagnostic ultrasound system of the second embodiment has the configuration shown in FIG. 10.

To be more specific, the diagnostic ultrasound system comprises an ultrasound probe 100 responsible for transmitting or receiving ultrasonic waves to or from a subject, and a main unit 101 for driving the ultrasound probe 100 and processing signals received by the ultrasound probe 100.

The ultrasound probe 100 is of a phased array type similarly to the one in the first embodiment. The main unit 101 has an ultrasonic-wave transmitter/receiver 110 connected to the ultrasound probe 100, and includes a phase detector 111, an A/D converter 112, a filter 113, a motion velocity analyzer 114, a DSC 115, a coloring unit 116, a D/A converter 117, and a color monitor 118 which are connected in that order in the output stage of the ultrasonic-wave transmitter/receiver 110.

The motion velocity analyzer 114 is connected to a blanking control unit 121 for blanking at least part of a color image of tissue motion which will be described later. Necessary information is fed to the blanking control unit 121 by an examining physician through an input unit 122.

The ultrasonic-wave transmitter/receiver 110 includes a transmitter/receiver 110a for driving the ultrasound probe 100 in cycles of a duration of a supplied rate pulse and for beam-forming echoes sent from the ultrasound probe 100 by delaying the echoes and adding them to each other, a rate pulse generator (RPG) 110b for supplying necessary information such as raster addresses to the transmitter/receiver 110a, and an envelope detector 110c for producing a B-mode image signal. The ultrasonic-wave transmitter/receiver 110 functions similarly to the one in the first embodiment.

In the output stage of the transmitter/receiver 110a, the phase detector 111, A/D converter 112, and filter 113 are connected in that order. These units function similarly to the phase detector 20 and filter 21 (having the capability of an A/D converter) in the first embodiment.

The motion velocity analyzer 114 includes a frequency analyzer 114a for analyzing frequencies of Doppler signals detected at sample points on a tomographic layer by performing autocorrelation or the like. The motion velocity analyzer 114 further includes a velocity arithmetic unit 114b for computing average frequencies (average velocities) of Doppler signals at the sample points using the results of the analysis, a variance arithmetic unit 114c for computing variances (spectral incoherences), and a power arithmetic unit 114d for computing the intensities (powers) of Doppler signals.

Figure 11:
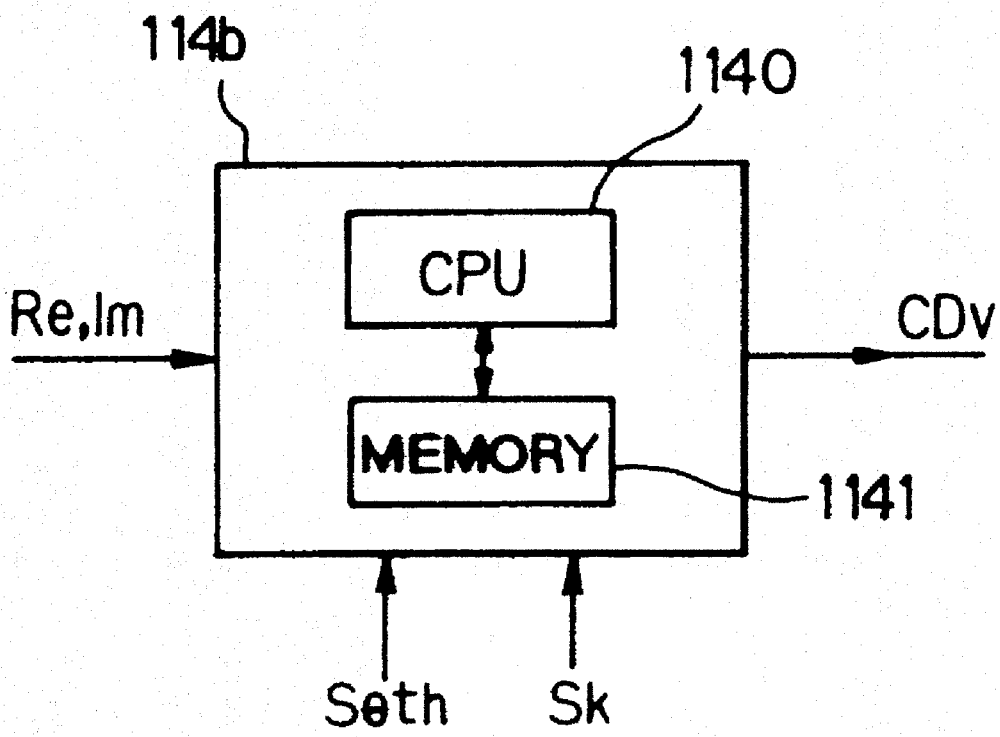
FIG. 11 is a block diagram showing a velocity arithmetic unit in the second embodiment.
Figure 12:
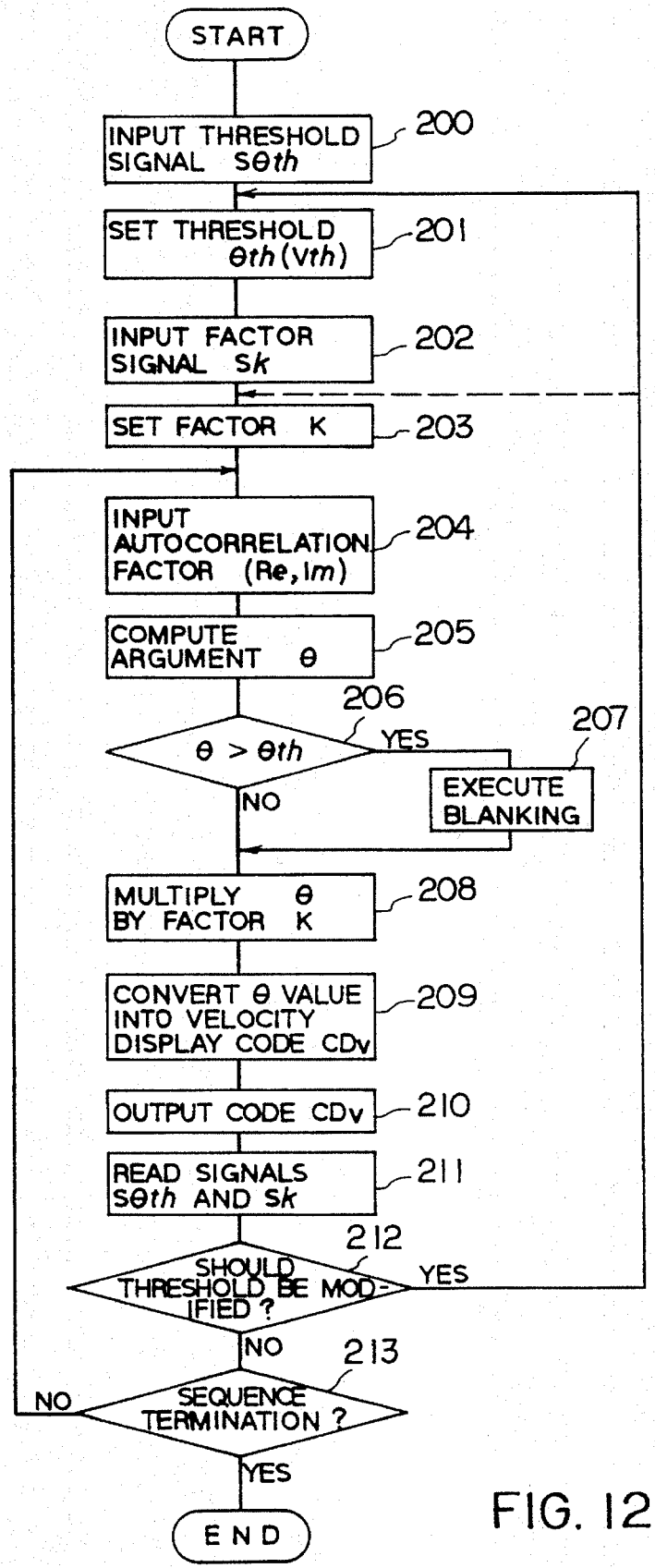
FIG. 12 is a flowchart describing an example of a sequence executed by the velocity arithmetic unit.
Figure 13:
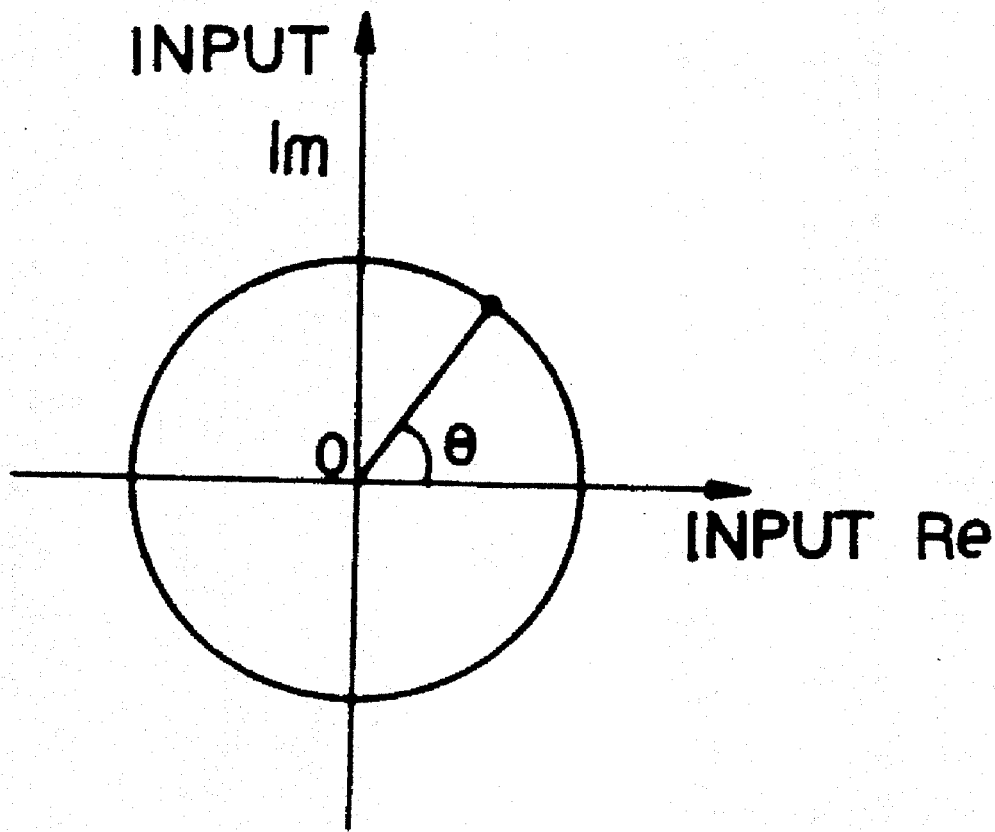
FIG. 13 is an explanatory diagram concerning output data supplied by a frequency analyzer.

The velocity arithmetic unit 114b in this embodiment includes, as shown in FIG. 11, a CPU 1140 and a memory 1141. A program that runs as described in FIG. 12 is pre-set in a given storage area in the memory 1141. The program is run automatically with the activation of the velocity arithmetic unit 114b. The velocity arithmetic unit 114b may be made by combining analog and digital electronic circuit elements in such a manner that they function to execute the sequence shown in FIG. 12.

The blanking control unit 1 21 interprets a signal supplied from the input unit 122, and, on the basis of the interpretation, supplies a threshold signal $S_{\theta th}$ representing a threshold $\theta_{th}$ of an argument θ required for blanking and a factor signal $S_K$ representing a scale conversion factor K to the velocity arithmetic unit 11b.

The DSC 115 inputs image data of a monochrome B-mode tomographic image sent from the envelope detector 110c as well as image data of a TDI image sent from the velocity arithmetic unit 114b, variance arithmetic unit 114c, and power arithmetic unit 114d, and produces frame image data in which the TDI image is superposed (synthesized with) on the B-mode image. The frame image data is sent to the coloring unit 116. The coloring unit 116 colors the pixels of the TDI image according to the velocity display codes, and sends the color frame image data to the color monitor 118 via the D/A converter 117.

The sequence executed by the velocity arithmetic unit 114b will be described in conjunction with FIG. 12.

Figure 14:
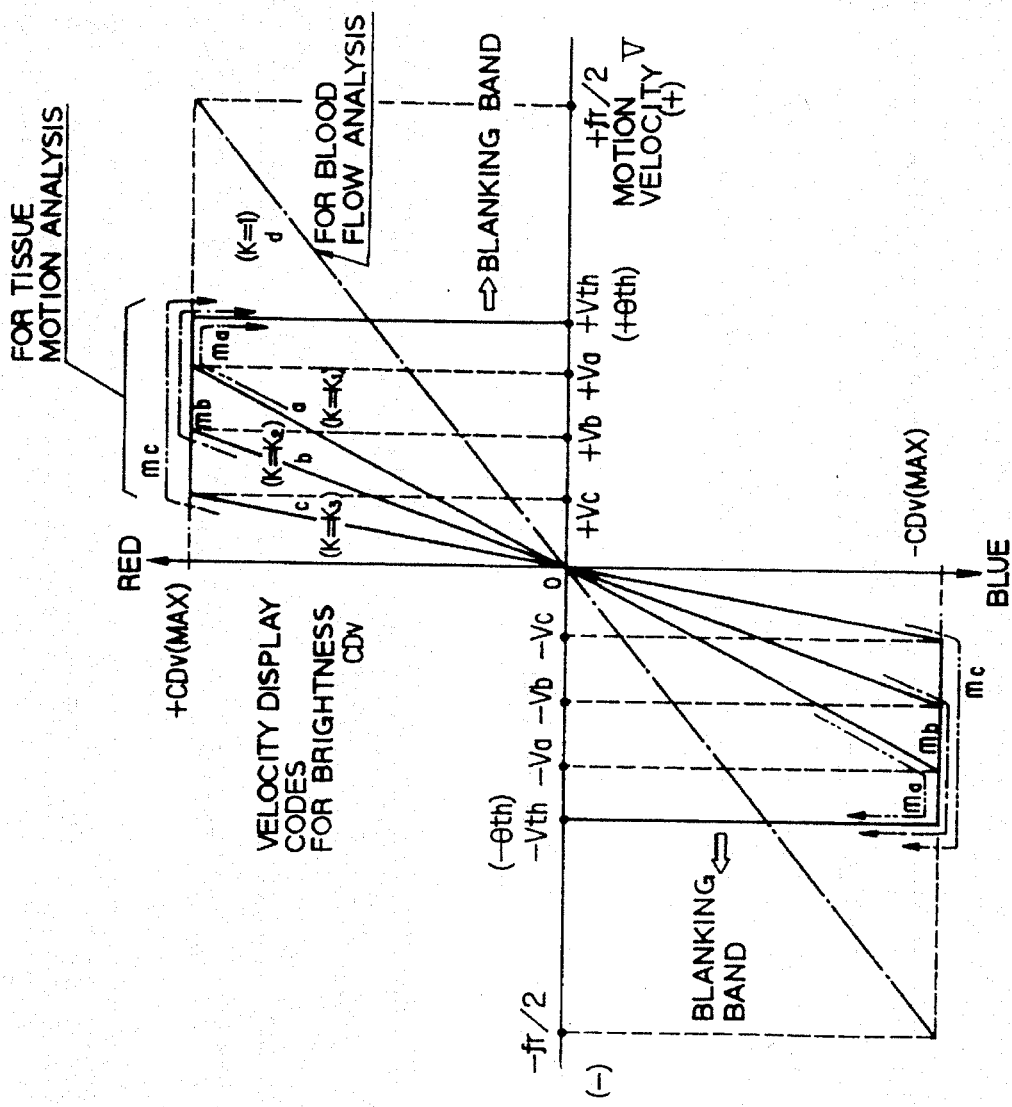
FIG. 14 shows an example of a velocity conversion scale.
Figure 15:
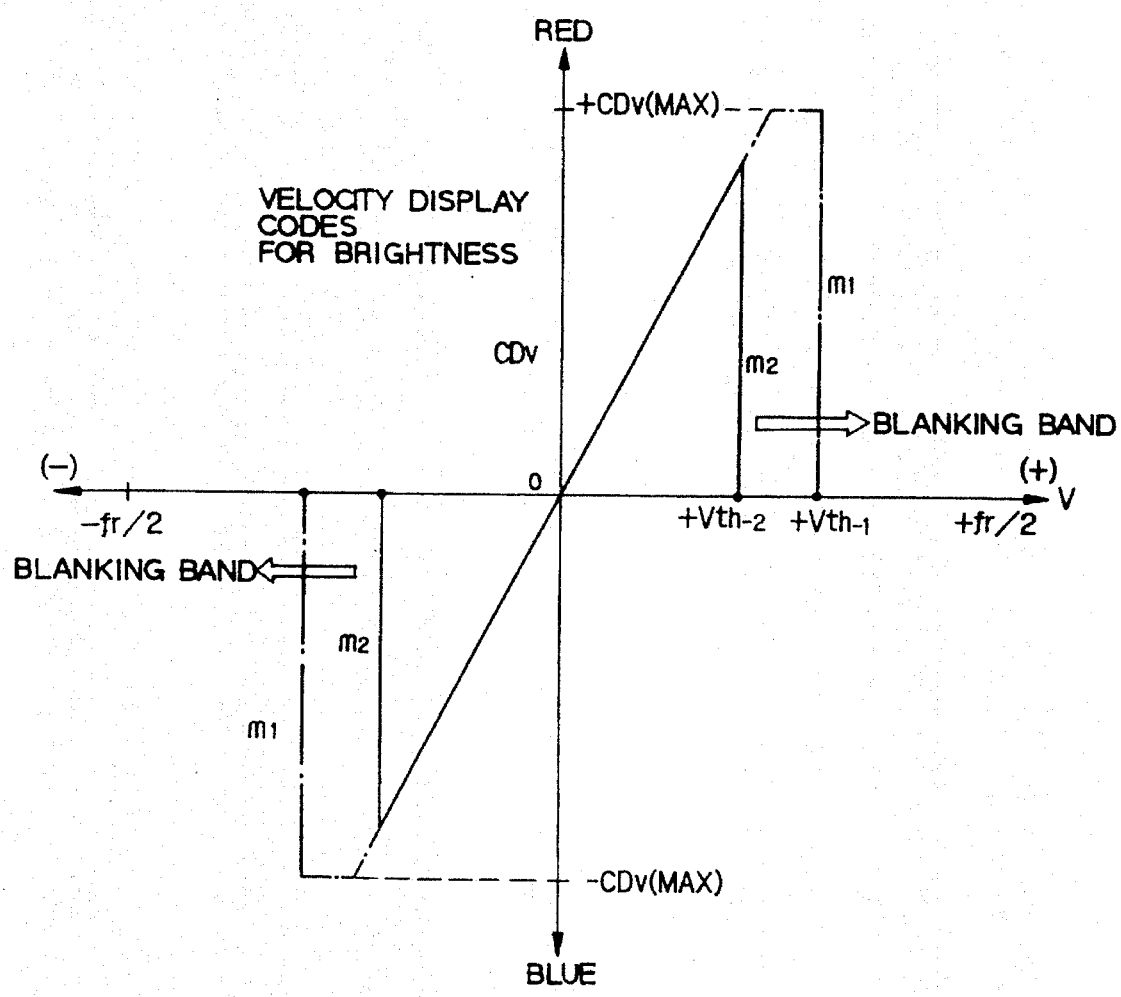
FIG. 15 is an explanatory diagram concerning an increase or decrease in size of a blanking band corresponding to a change in velocity threshold.

The CPU 1140 in the velocity arithmetic unit 114b first reads the threshold signal $S_{\theta th}$ supplied from the blanking control unit 121 at step 200. At step 201, the CPU 1140 stores the threshold $\theta_{th}$ represented by the threshold signal $S_{\theta th}$. The velocity arithmetic unit 114b inputs, as described later, for example, the factors Re and Im (complex numbers) among autocorrelation factors Re, Im and $P_0$ for average frequencies of Doppler signals (average velocities) resulting from analysis made by the frequency analyzer 114a, and calculates an argument θ indicating a point on a unit circle on a complex plane and corresponding to a motion velocity of a tissue (See FIG. 13). The threshold ($\theta_{th}$ is therefore equivalent to a threshold $V_{th}$ of a motion velocity V (indicating a Doppler shift frequency) as shown in FIG. 14.

The CPU 1140 then passes control to step 202, and reads the factor signal SK representing the scale conversion factor K (>1) for use in enhancing the ability to display a TDI image from the blanking control unit 121. At step 203, the scale conversion factor K represented by the factor signal $S_K$ is stored, When the factor K equals to 1, blood flow velocity analysis is designated.

At step 204, the CPU 1140 inputs, for example, the autocorrelation factor (Re, Im) provided by the frequency analyzer 114a. At step 205, the CPU 1140 computes the argument θ corresponding to the velocity V of tissue motion mentioned above. The argument θ has a value indicating that the scale conversion factor K is 1; that is, that blood flow velocity analysis is designated. The value of the argument θ varies according to a straight line (velocity conversion scale) indicated with a dot-dash line d in FIG. 14. In FIG. 14, the abscissa indicates the motion velocity V and the ordinate indicates the velocity display code $CD_v$ (for example, logical data of 8 bits long) representing a brightness level used as a gradation level of red (for a motion approaching the probe) or blue (for a motion receding from the probe). In FIG. 14, various lines or velocity conversion scales in accordance with the present invention may be plotted as described later. The straight line d manifests a velocity conversion scale to be used for blood flow velocity analysis. The velocity conversion scale d is, as already known, such that velocity display codes $CD_v$ having a continuous change are assigned to all the velocities V within aliasing-prone velocities indicated with a band of ±fr/2.

At step 206, the CPU 1140 determines whether the argument θ computed at step 205 exceeds the threshold $\theta_{th}$ set at step 201 (that is, whether the V value exceeds the $V_{th}$ threshold). When the result of the determination is in the affirmative (θ>$\theta_{th}$), control is passed to step 207. A blanking command is issued in order to blank pixels rendering the motion velocity corresponding to the argument θ that exceeds the threshold $\theta_{th}$ (V>$V_{th}$). By performing blanking, the velocity display codes $CD_v$ assigned to the pixels concerned are forcibly set to a value of 0, 0, ..., 0 (blank code) meaning that the V value is 0.

When the blanking command terminates or when the result of the determination made at step 206 is in the negative (θ<$\theta_{th}$), control is passed to step 208. At step 208, the scale conversion factor K (>1) set at step 203 is multiplied by the argument θ computed at step 205.

With the multiplication of K by θ, the argument θ corresponding to the velocity V of tissue motion is weighted to enhance a low-velocity band of a TDI image signal. For example, a velocity conversion scale whose scale conversion factor K equals to a $K_1$ value (that is larger than 1 or, for example, 4) is plotted as a line a but not plotted as the straight line d indicating that blood flow analysis is designated. Even when the argument θ(=0) having undergone blanking is multiplied by the factor K, the product is zero. The velocity conversion scale a that is an example of a velocity conversion scale for tissue Doppler imaging is, as shown in FIG. 14, plotted as a characteristic line according to which velocity codes equivalent to all set brightness levels of display colors; red and blue are assigned to a range of V=±Va (for example, ±fr/8). A range of Va≧|V|≧$V_{th}$ is assigned velocity display codes ±$CD_{v(MAX)}$ associated with maximum brightnesses, or in other words, saturated colors. With the V values equal to ±$V_{th}$, the characteristic line a falls to the axis of abscissas indicating a color of black.

Another examples of velocity conversion scales are plotted as characteristic lines b and c in FIG. 14, wherein the scale conversion factor K by which the argument θ is multiplied is set to a $K_2$ value (which is larger than the $K_1$ value and, for example, 8) and a $K_3$ value (which is larger than the $K_2$ value and, for example, 16) respectively. According to the velocity conversion scale b, the value of the velocity display code $CD_v$ increases linearly in a range of V=±Vb (for example, ±fr/12). A range of Vb≧|V|≧$V_{th}$ is assigned saturated colors or maximum velocity display codes ±$CD_{v(MAX)}$ associated with maximum brightnesses of red and blue. For the other velocity conversion scale c, the value of the velocity display code $CD_v$ increases linearly in a range of V=±Vc (for example, ±fr/16). A range of Vc≧|V|≧$V_{th}$ is assigned the saturated colors or maximum velocity display codes ±$CD_{v(MAX)}$ associated with maximum brightnesses. In either of the scales b and c, the characteristic line falls with the V value given as |V|≧Vth because of the effect of blanking. As mentioned above, the slope of the straight line section of a characteristic line of a velocity conversion scale gets larger proportionally to the value of the factor K serving as a multiplier. The ability to render a low-velocity band according to gradations is enhanced proportionally to the value of the scale conversion factor K.

Upon completion of multiplication to be performed for tissue Doppler imaging using the scale conversion factor K as a multiplier, the CPU 1140 passes control to step 209 in FIG. 12, and converts a product of the argument θ (corresponding to the velocity V) by the factor K into a velocity display code $CD_v$. The conversion is achieved by referencing a storage table which is pre-set in the memory 1141 and in which the values of the argument θ are placed in one-to-one correspondence with velocity display codes $CD_v$ (each of which is, for example, 8 bits long). At step 210, the velocity display code $CD_v$ resulting from the conversion is fed to the DSC 115.

At step 211, the threshold signal Sθth and factor signal $S_K$ are read again. At step 21 2, it is determined whether both or either of the threshold $θ_{th}$ of the argument θ represented by the threshold signal $S_{θth}$ and the factor K represented by the factor signal $S_K$ shonuld be modified. If the values are modified, control is returned to step 201 or 203. If the threshold $θ_{th}$ and factor K are not modified but blanking is continued, control is returned to step 204 via step 213. Blanking is controlled as described previously.

Echoes reflected from living tissues to which an ultrasound beam is transmitted from the ultrasound probe 100 are returned to the probe 100. The echoes are converted into received signals with magnitudes of electricity by the probe 100, received by the transmitter/receiver 110a, and then subjected to orthogonal phase detection by the phase detector 111. Signal components having Doppler shifts that are induced by tissue motion are extracted from the detected signals by means of the filter 113. The Doppler signals still containing clutter components are sent to the frequency analyzer 114a. The results of the frequency analysis are sent to the velocity arithmetic unit 114b, variance arithmetic unit 114c, and power arithmetic unit 114d, whereby intended values relevant to tissue motion are computed. In the power arithmetic unit 114d, the computation of $K\log_{10}P_0$ is carried out (K is a constant).

Assuming that commands are issued to the velocity arithmetic unit 114b via the input unit 122 and blanking control unit 121 in order to specify the threshold $θ_{th}$ of the argument θ (that is, the threshold $V_{th}$ of the velocity V of tissue motion) as shown in FIG. 14 and to set the scale conversion factor K required for tissue Doppler imaging to a $K_2$ value (line b), the characteristic line indicated with a dot-dash line mb in FIG. 14 is selected for conversion into codes.

When an average velocity (a product of K by θ) of tissue motion computed for enhancement of a TDI image is within a low-velocity range of $|V|<±Vb$, all permissible velocity display codes CDV are employed. When the velocity V is within a range of $±Vb≦|V|<±V_{th}$, maximum velocity display codes $±CDV_{(MAX)}$ associated with maximum brightnesses are assigned to saturated colors. Velocities defined with $±V_{th}≧|V|$ are assigned a blank code.

As mentioned above, the results of motion velocity analysis containing average velocity data, which have undergone blanking, are sent to the DSC 115. The DSC 115 is also provided with B-mode image data by the envelope detector 110c. The motion velocity information is superposed on the B-mode image. The superposed frame image data is colored by the coloring unit 116, and then displayed on the color monitor 118. The display image has the motion velocity information concerning a color image of tissue motion superposed on the background of the monochrome B-mode image. Pixels rendering velocities exceeding a designated $V_{th}$ value are blanked at step 207 in FIG. 12 and therefore not displayed in color. In other words, color information is not superposed on pixels rendering a high-velocity band indicated with $±V_{th}≦|V|$, and only the B-mode image serving as the background is visible to an examining physician.

When the velocity threshold $V_{th}$ (practically, the threshold $θ_{th}$ of the argument θ) to be specified in order to cut off a high-frequency band is set to an appropriate value, tissue motion such as of cardiac muscle motion that is visualized with a maximum brightness without any change in gradation can be limited to the smallest possible area (smallest number of pixels). This results in an easy-to-see screen. It is therefore substantially avoidable that the maximum-brightness image unnecessary for tissue motion analysis interferes with diagnosis. This contributes to improvement of diagnostic efficiency (or to reduction of time and labor required for diagnosis).

A background image (monochrome B-mode image) appears in place of the maximum-brightness image. Thus, another information required for diagnosis becomes available.

Since the velocity conversion scales a, b, and c (See FIG. 14) characteristic of enhancing a low-velocity band are employed, low motion velocities suggesting necrotic tissues are readily discernible. This leads to improvement of the ability to diagnose whether a ROI is normal or abnormal.

In this embodiment, the threshold $V_{th}$ of the motion velocity V can be set irrespectively to the velocity conversion scale a (b or c). The maximum brightnesses $±CD_{v(MAX)}$ of red and blue to be allowed to appear in a monitor screen can be adjusted optimally to the same velocity conversion scale a (b or c) (or, in other words, to the same low-velocity enhancement function). Depending on the threshold $V_{th}$ and scale conversion factor K, as indicated with a dot-dash line $m_1$ in FIG. 15, images with maximum brightnesses associated with maximum gradation levels may be allowed to appear in a monitor screen. Alternatively, as indicated with a solid line $m_2$ in FIG. 15, a TDI color image alone whose brightnesses have not reached to the maximum values may be blanked.

In this embodiment, a plurality of velocity conversion scales a, b, and c are pre-prepared for tissue motion analysis and selectively used according to a diagnostic purpose (See steps 202 and 211 in FIG. 12). This results in a highly general-purpose system. Virtual lines ma and mc in FIG. 14 present another examples of velocity conversion characteristic lines in which the velocity threshold $V_{th}$ is set to a fixed value.

Third Embodiment

The third embodiment of the present invention will be described in conjunction with FIGS. 16 to 20. In a diagnostic ultrasound system in accordance with the third embodiment, the aforesaid blanking of a high-velocity band of tissue motion signals is executed after velocity display codes are computed so that a low-velocity band will be enhanced. For the third embodiment and thereafter, component elements identical to those in the second embodiment will be assigned the same reference numerals. The description on the identical component elements will be omitted or summarized.

Figure 16:
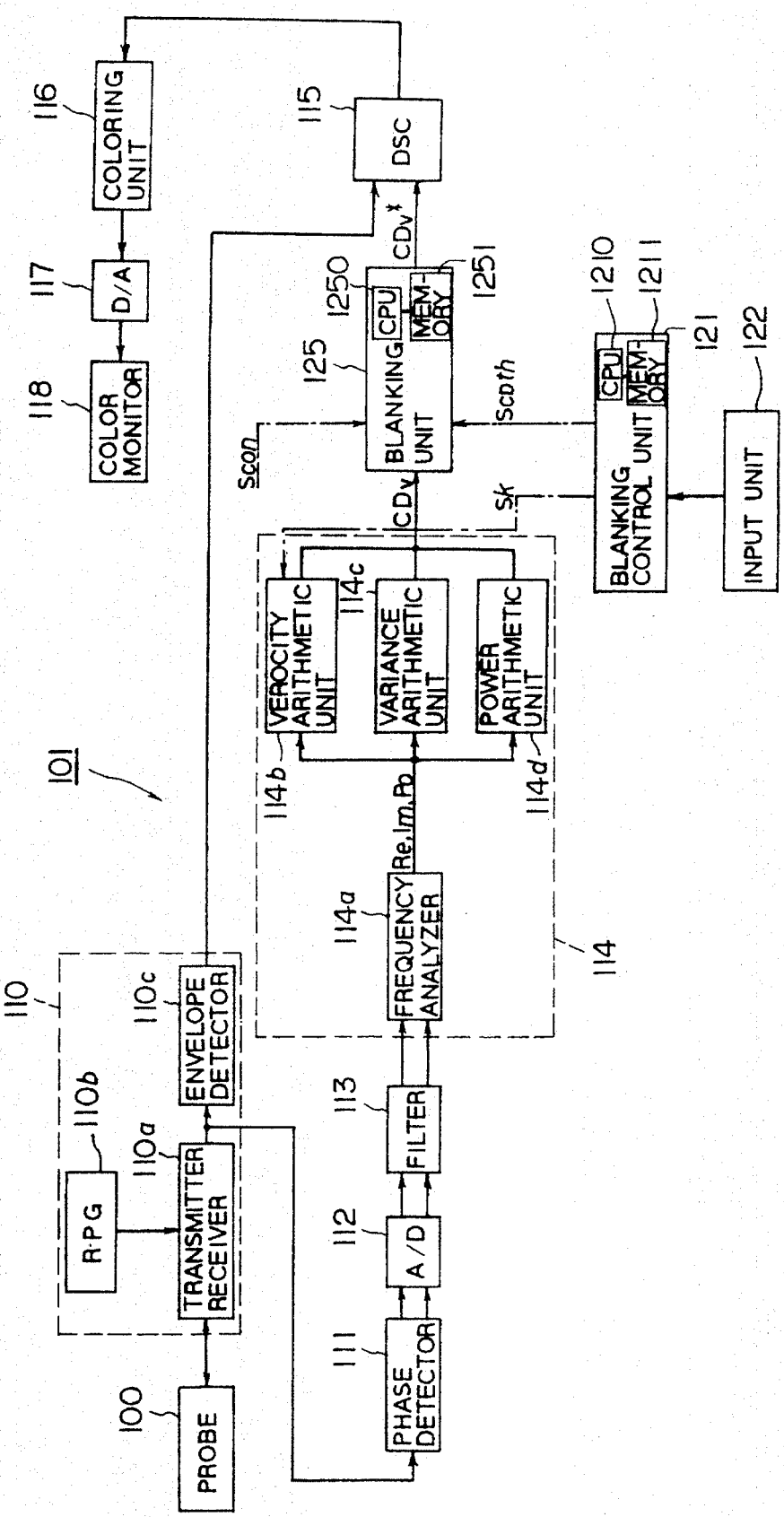
FIG. 16 is a block diagram showing a diagnostic ultrasound system in accordance with the third embodiment of the present invention.

FIG. 16 is a block diagram showing a diagnostic ultrasound system of the third embodiment. A blanking unit 125 is interposed between the motion velocity analyzer 114 and DSC 115. The aforesaid factor signal $S_K$ alone is supplied from the blanking control unit 121 to the aforesaid velocity arithmetic unit 114b. A threshold signal $S_{CDth}$ representing a threshold of a velocity display code is supplied to the blanking unit 125.

The blanking control unit 121 has the capability of a computer, including a CPU 1210 and a memory 1211. The CPU 1210 executes the sequence described in FIG. 17. The CPU 1140 in the velocity arithmetic unit 114b executes the sequence described in FIG. 18. The blanking unit 125 includes a CPU 1250 and a memory 1251. The CPU 1250 executes the sequence described in FIG. 19.

Figure 17:
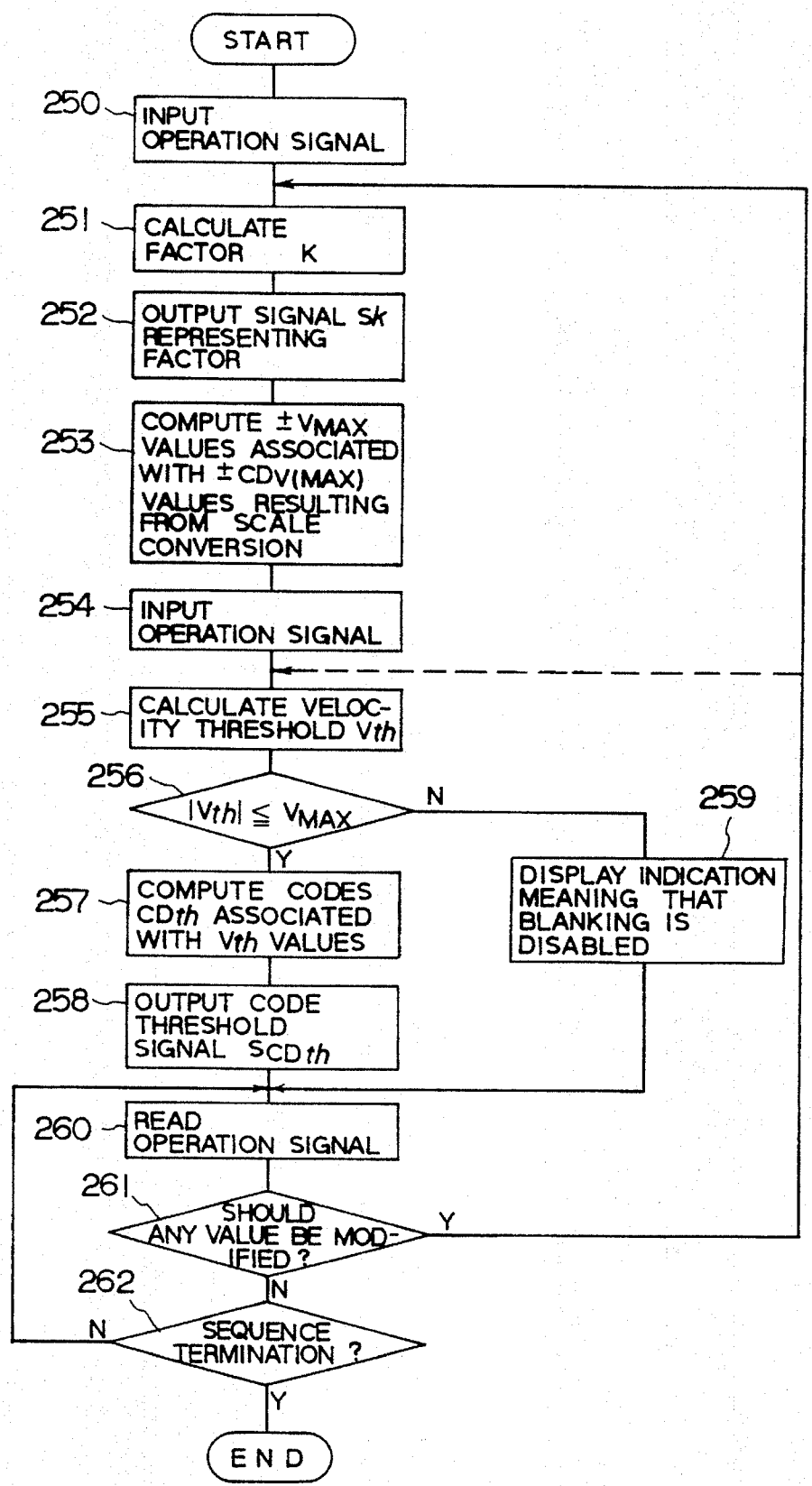
FIG. 17 is a flowchart describing an example of a sequence executed by a blanking control unit in the third embodiment.

To begin with, the actions of the blank control unit 121 will be described in conjunction with FIG. 17. The CPU 1210 calculates a scale conversion factor K on the basis of an operation signal entered at the input unit 122 at steps 250 and 251. The CPU 1210 then outputs a factor signal $S_K$ representing the calculated scale conversion factor K to the velocity arithmetic unit 114b (step 252). At step 253, velocities $\pm V_{MAX}$ represented by velocity display codes $\pm CD_{v\text{-}(MAX)}$ that are associated with maximum brightnesses and derived from a velocity conversion scale which is weighted with the K value and designed for blood flow analysis are computed (See FIG. 20). The computation of the $\pm V_{MAX}$ values may be assigned to the velocity arithmetic unit 114b, and then the computed values may be returned from the velocity arithmetic unit 114b.

Figure 20:
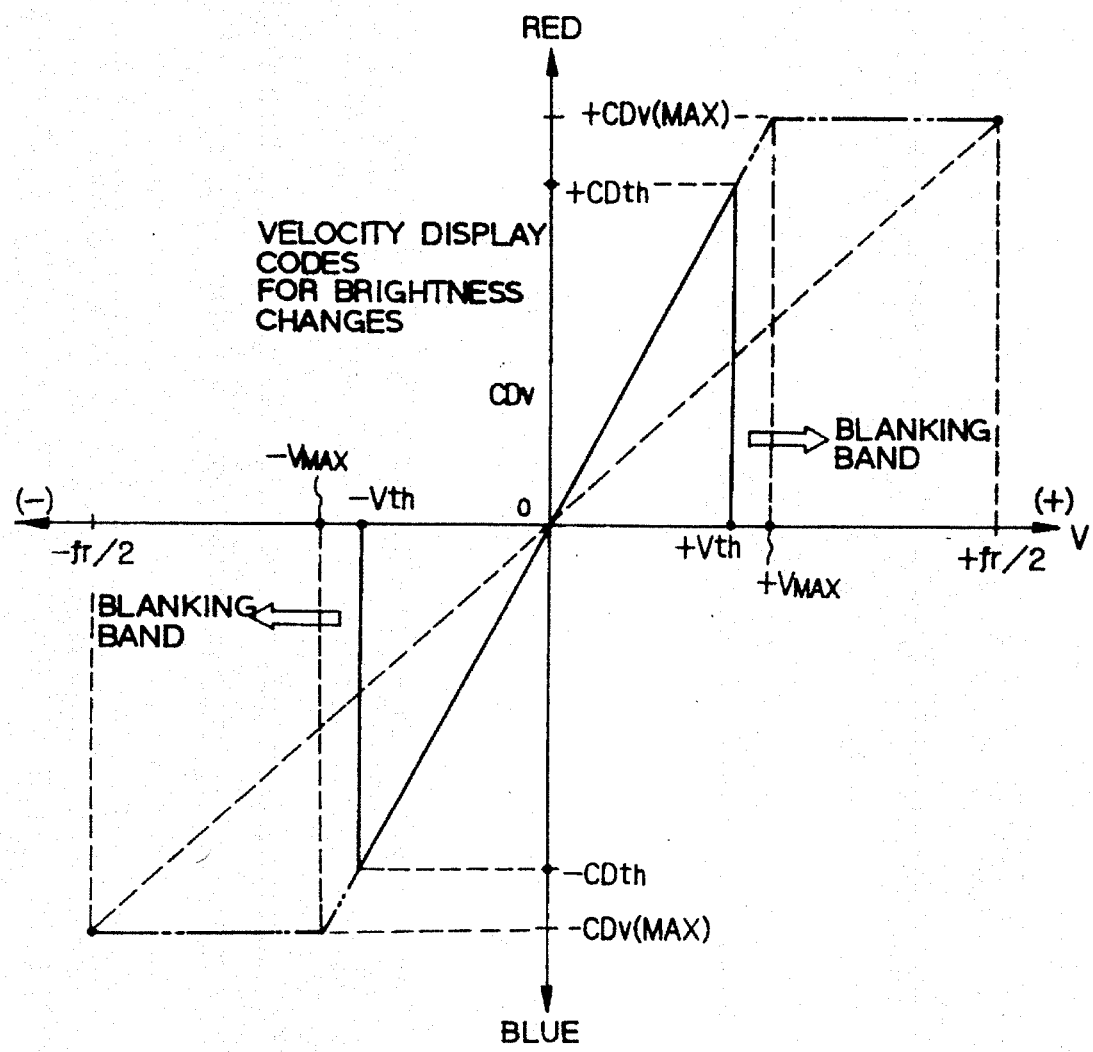
FIG. 20 shows an example of a velocity conversion scale in the third embodiment.

The CPU then reads an operation signal entered at the input unit 122 at step 254, and computes the velocity threshold $V_{th}$ desired by an examining physician at step 255 (See FIG. 20). The velocity threshold has no direct relation to the argument θ, for the velocity threshold $V_{th}$ is supposed to define thresholds for the already-converted velocity display codes $CD_v$ supplied from the velocity arithmetic unit 114b.

Based on the velocity threshold Vth, it is determined at step 256 whether $|V_{th}|>V_{MAX}$ is established. If the result of the determination is in the affirmative or if $-V_{MAX} \leq Vth \leq +V_{MAX}$ is established, a threshold $CD_{th}$ of a velocity display code corresponding to the threshold $V_{th}$ is computed (See FIG. 20) (step 257). A code threshold signal $S_{CDth}$ representing the threshold $CD_{th}$ is then supplied to the blanking unit 125 (step 258). By contrast, if the result of the determination made at step 256 is in the negative or if $|V_{th}|>V_{MAX}$ is established, an indication meaning that blanking is disabled is displayed on the monitor 118 by means of the DSC 115 (See the signal $S_{un}$ in FIG. 16).

After the processing of steps 259 and 258 is completed, an attempt is made at step 260 to read an operation signal entered at the input unit 122. At step 261, it is determined whether the examining physician wants to modify both or either of the scale conversion factor K and velocity threshold $V_{th}$. If the result of the determination is in the affirmative, control is returned to step 251 or 255 and the processing is rerun. If the result of the determination made at step 261 is in the negative, it is determined at step 262 whether the sequence terminates. If the sequence continues, the processing of steps 260 to 262 is rerun and a standby state is set up.

Figure 18:
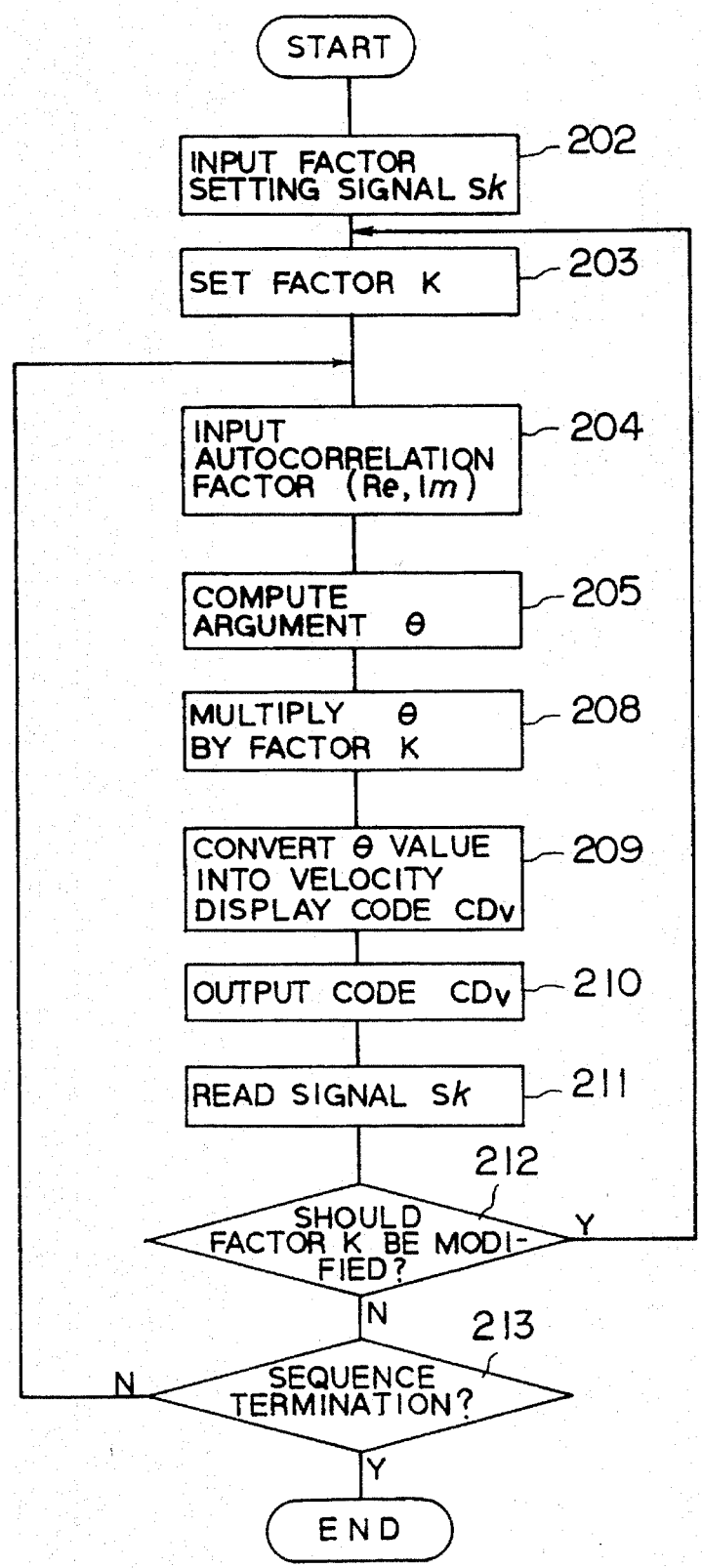
FIG. 18 is a flowchart describing an example of a sequence executed by a velocity arithmetic unit in the third embodiment.

The subsequent actions of the velocity arithmetic unit 114b will be described in conjunction with FIG. 18. The actions are identical or equivalent to the corresponding steps bearing the same reference numerals in FIG. 12. Steps 202,201,206, and 207 in FIG. 12 are excluded, though. In response to a command specifying the scale conversion factor K and being issued from the blanking control unit 121, a velocity display code $CD_v$ that is weighted in order to enhance a low-velocity band is supplied to the blanking processor 125.

Figure 19:
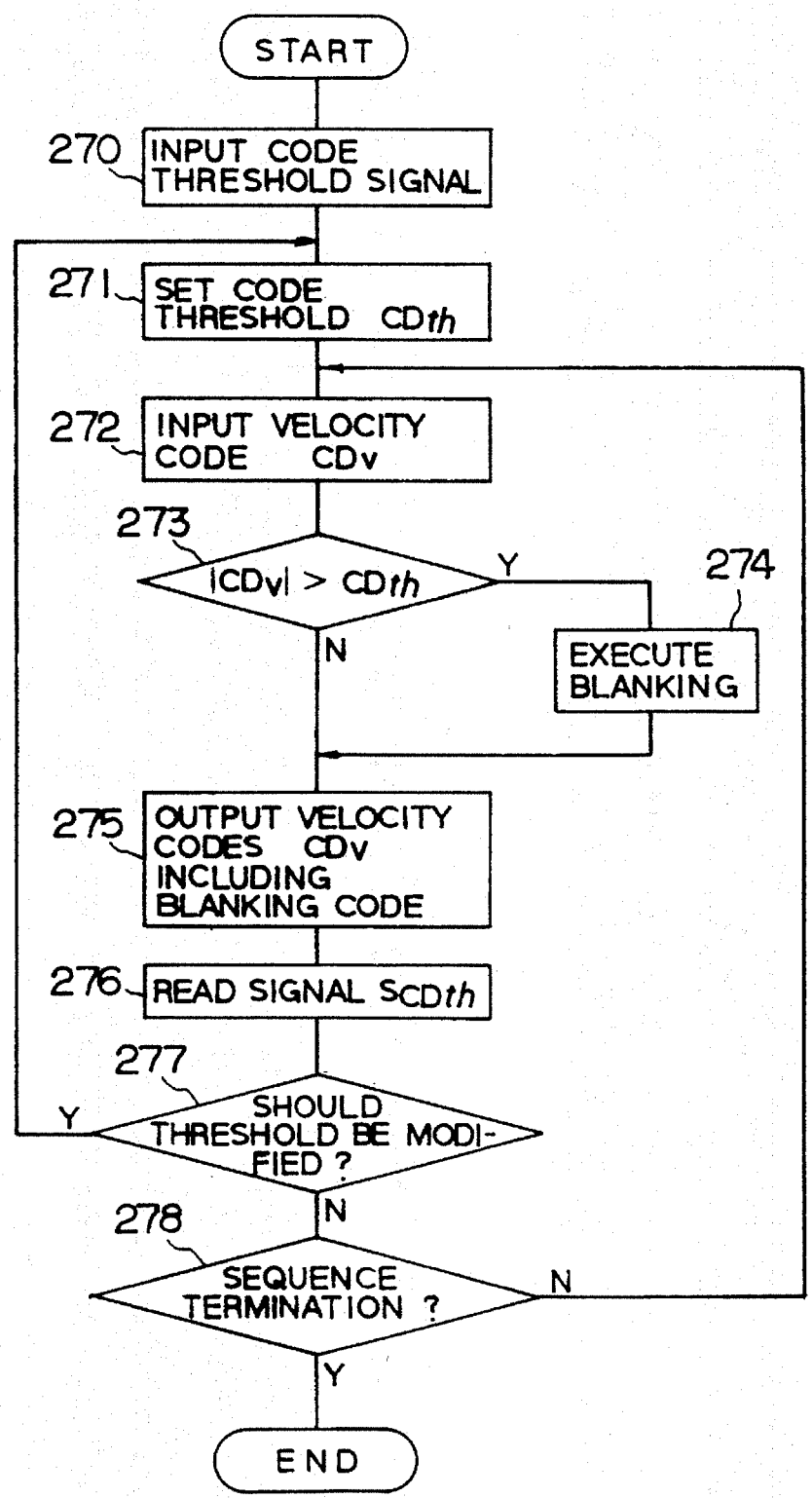
FIG. 19 is a flowchart describing an example of a sequence executed by a blanking unit in the third embodiment.

The actions of the blanking unit 125 will be described in conjunction with FIG. 19. A CPU 1250 in the blanking unit 125 first reads a code threshold signal $S_{CDth}$ sent from the blanking unit 121 at step 270, and sets the threshold $CD_{th}$ of a velocity display code at step 271. The velocity display code $CD_v$ sent from the velocity arithmetic unit 114b is read at step 272, and it is determined at step 273 whether $|CD_v|>CD_{th}$ is established. If the result of the determination is in the affirmative (the absolute value of the sent code $CD_v$ exceeds the threshold $CD_{th}$), control is passed to step 274. Blanking is then performed on the velocity display code $CD_v$. Thus, a blank code is forcibly assigned to each of pixels rendering velocities V associated with codes $CD_v$ whose absolute values exceed the threshold $CD_{th}$.

If the result of the determination made at step 273 is in the negative or $|CD_v| \leq CD_{th}$ is established, the velocity display code $CD_v$* (including the blanking code) having undergone blanking at step 274 is supplied to the DSC 115 (step 275).

At step 276, the CPU 1250 attempts to read a code threshold signal $S_{CDth}$ that may be supplied from the blanking unit 125. At step 277, the CPU 1250 determines whether the examining physician wants to modify the threshold $CD_{th}$. For modifying the threshold $CD_{th}$, control is returned to step 271. For leaving the threshold $CD_{th}$ intact, it is determined at step 278 whether the sequence terminates. If the sequence does not terminate, control is returned to step 272. The aforesaid processing is rerun.

The blanking unit 125 is not illustrated in particular. For observing both or either of a velocity variance and a power independently, these values are supplied directly to the DSC 115. For observing the values together with a velocity V, the velocity V (that is, a velocity display code $CD_v$) is given priority, and pixels to which velocity display codes $CD_v$ exceeding the threshold $CD_{th}$ are assigned are blanked. The processing is executed in response to a command signal $S_{con}$ entered at a console that is not shown.

The blanking control unit 121, velocity arithmetic unit 114b, and blanking unit 125 act as described above. As shown in FIG. 20, only when the threshold $V_{th}$, which are used for blanking and designated by the examining physician, is within a range of $\pm V_{th}$ associated with maximum gradation levels of the gradation scale in which a low-velocity band of tissue motion signals is enhanced, pixels rendering velocities exceeding the velocity thresholds $\pm V_{th}$ are blanked automatically. Thus, the same effect as the one of the second embodiment is exerted. Even when the value of the scale conversion factor K is modified, blanking is executed on a constant basis.

In this embodiment, however, velocity display codes $CD_v$ succeeding the velocity display codes representing velocities $\pm V_{MAX}$ do not have any progressive change. When an examining physician designates values exceeding the $\pm V_{MAX}$ values as the thresholds $\pm V_{th}$, the fact is reported to the examining physician but blanking is not enabled. An examining physician need not pay special attention to what $\pm V_{MAX}$ values are set for low-velocity band enhancement but can designate any values as the thresholds $\pm V_{th}$. Thus, operation is easy.

Figure 21:
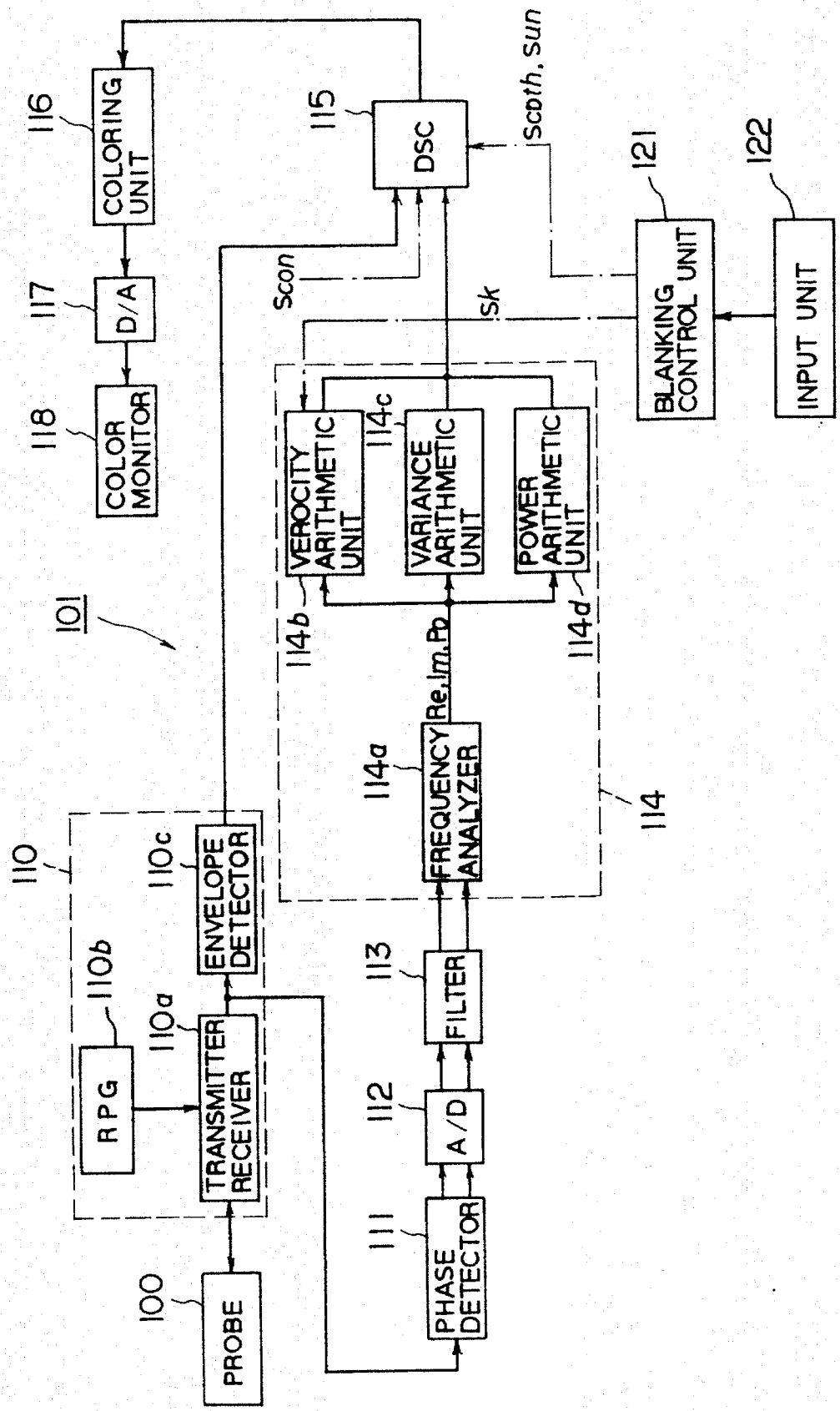
FIG. 21 is a block diagram showing a diagnostic ultrasound system in accordance with a variant of the present invention.

The capability of the blanking unit 125 may, as shown in FIG. 21, be given to the DSC 130. In this case, the code threshold signal $S_{CDth}$ and other control signals $S_{un}$ and $S_{con}$ are fed to the DSC 130. The DSC 130 blanks velocity display codes $CD_v$ with respect to a code threshold $CD_{th}$ associated with a velocity threshold $V_{th}$ in the same manner as that described previously, and superposes image data containing tissue motion information on B-mode data. Thus, an appropriate velocity threshold $V_{th}$ ($CD_{th}$) can be set for a low-velocity band indicating velocities that are represented with velocity display codes $CD_v$ having a progressive change. The same blanking effect as that in the third embodiment can be exerted.

Fourth Embodiment

In the aforesaid second and third embodiments, thresholds for blanking can be set irrespectively of a velocity conversion scale for use in low-velocity band enhancement. The thresholds (that is, blanking bands) can be determined at the same time of setting a velocity conversion scale. Subsequent embodiments provide diagnostic ultrasound systems in which this idea is implemented.

The fourth embodiment of the present invention will be described with reference to FIGS. 22 to 24.

Figure 22:
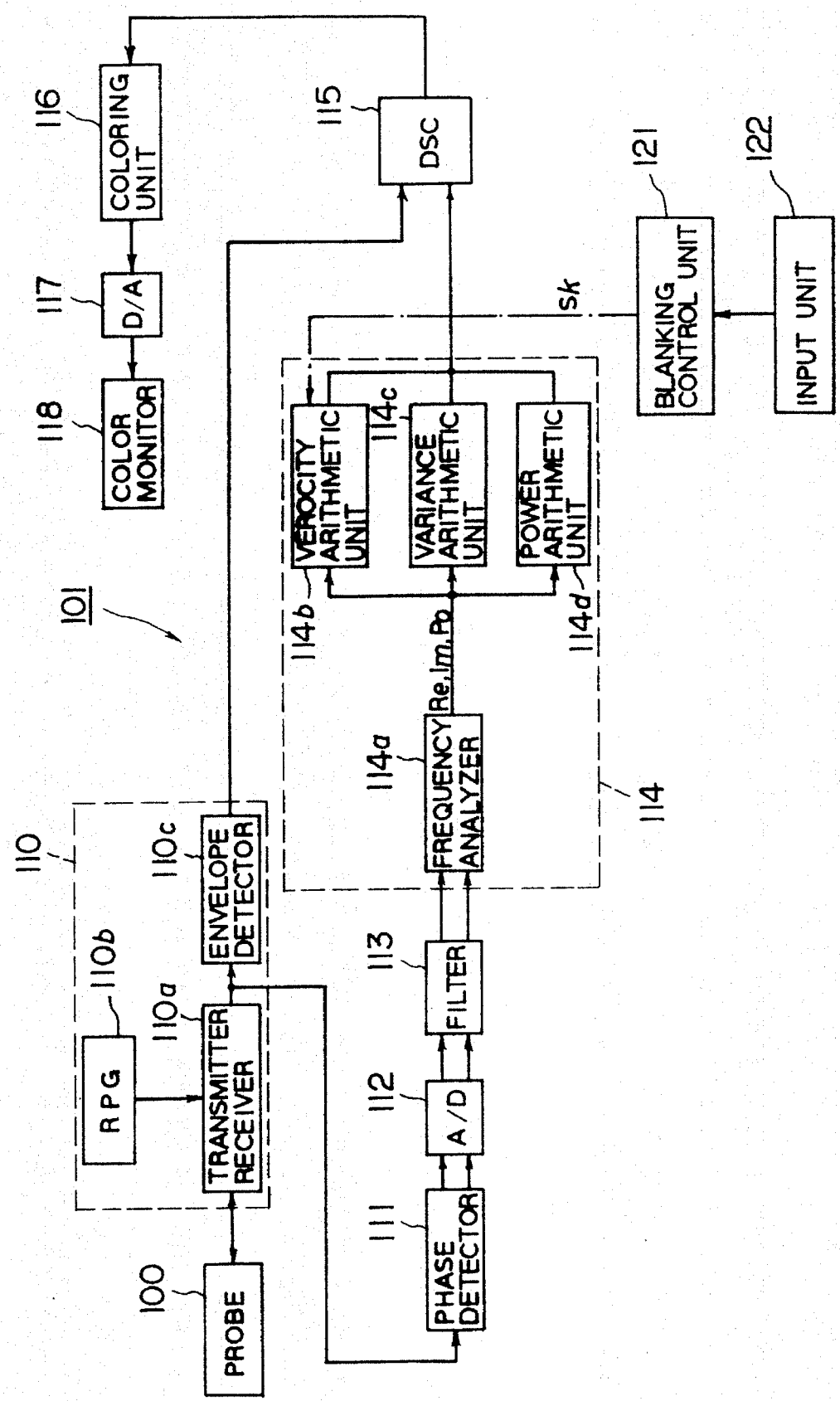
FIG. 22 is a block diagram showing a diagnostic ultrasound system in accordance with the fourth embodiment of the present invention.

A diagnostic ultrasound system shown in FIG. 22 has the aforesaid velocity arithmetic unit 114b. The CPU 1140 in the velocity arithmetic unit 114b executes the sequence shown in FIG. 23. Only the factor signal $S_K$ representing a factor for use in low-velocity band enhancement is fed from the blanking control unit 121.

Figure 23:
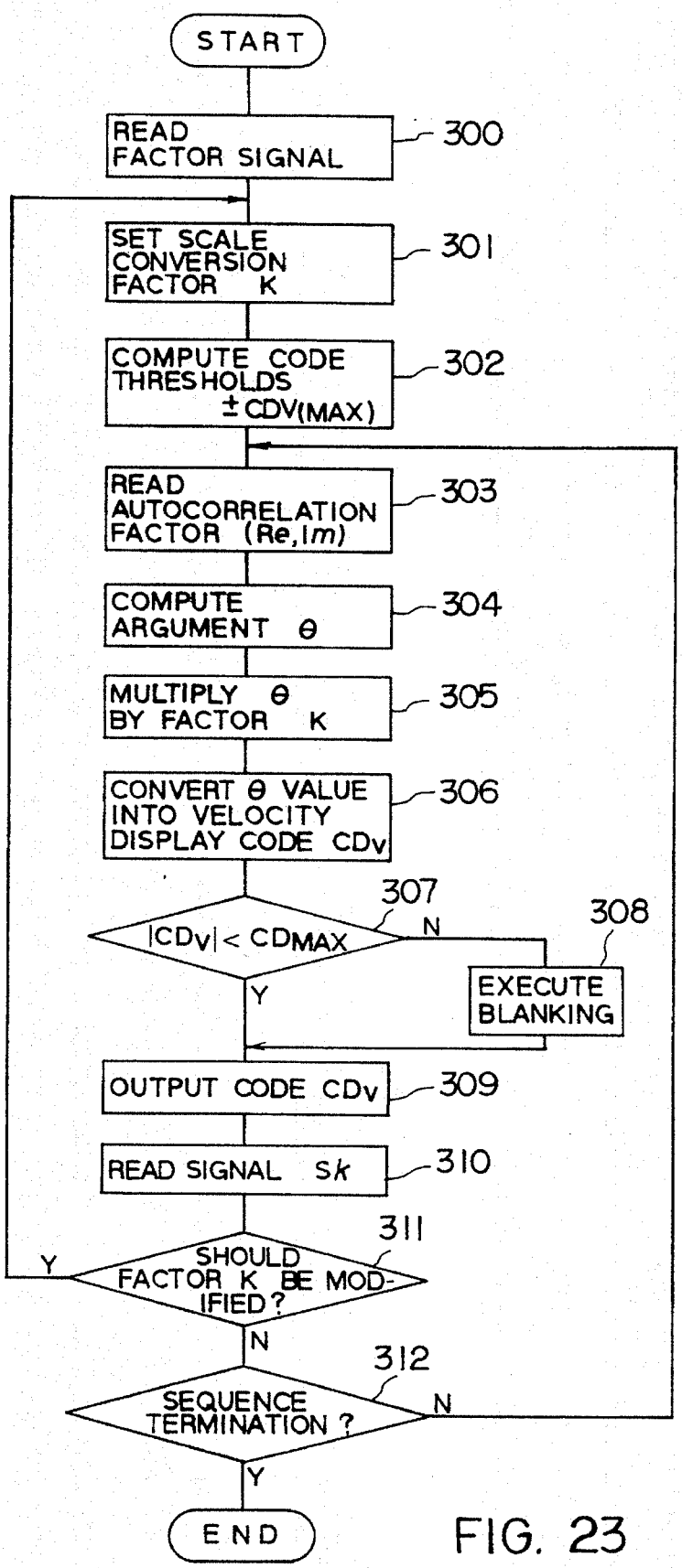
FIG. 23 is a flowchart describing a sequence executed by a velocity arithmetic unit in the fourth embodiment.
Figure 24:
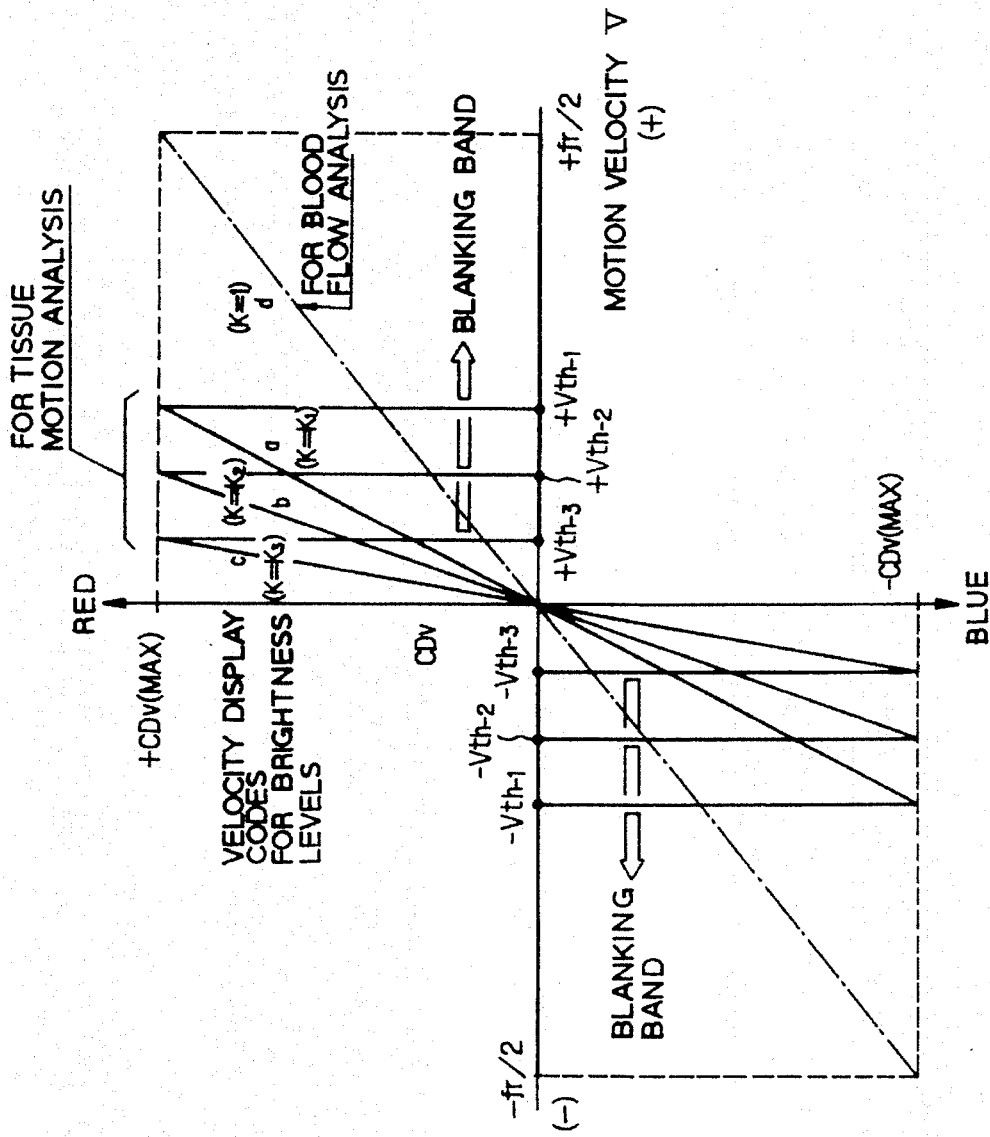
FIG. 24 shows an example of velocity thresholds that define blanking bands and depend on velocity conversion scales.

In FIG. 23, the CPU 1140 in the velocity arithmetic unit 114b executes the processing of steps 300 and 301 (corresponding to steps 202 and 203 in FIG. 12), and then computes code thresholds $\pm CD_{v(MAX)}$ equivalent to maximum highest gradation levels provided by a velocity conversion scale (See lines a to c in FIG. 24) at step 302. Thereafter, the processing of steps 303 and 304 (corresponding to steps 204 and 205 in FIG. 12) is executed. According to the sequence shown in FIG. 23, as soon as an argument θ is specified at step 304, the processing of steps 305 and 306 (corresponding to steps 208 and 209 in FIG. 12) is executed. The CPU 1140 then passes control to step 307, and uses the code thresholds $\pm CD_{v(MAX)}$ to determine whether the absolute value of a velocity display code $CD_v$ is larger than the $CD_{v(MAX)}$ value.

The determination is made on the assumption that tissue motion signals indicating velocities exceeding those associated with maximum gradation levels are blanked. Depending on the values of maximum gradation levels provided by a velocity conversion scale that has been weighted by the K value, a velocity threshold value $V_{th}$ for blanking is specified automatically. In short, when a velocity conversion scale for low-velocity band enhancement is produced, velocity thresholds are determined at the same time. For example, in the example shown in FIG. 24, when a velocity conversion scale a whose scale conversion factor K is set to a $K_1$ value (larger than 1) is employed, velocity thresholds $\pm V_{th-1}$ are adopted. When a velocity conversion scale b whose scale conversion factor K is set to a $K_2$ value (larger than $K_1$) is employed, velocity thresholds $\pm V_{th-2}$ are adopted. When a velocity conversion scale c whose scale conversion factor K is set to a $K_3$ value (larger than $K_2$) is employed, velocity thresholds $\pm V_{th-3}$ are adopted.

If the result of the determination made at step 307 is in the affirmative or if "$CD_v|<CD_{v(MAx)}$ is established, control is passed to step 309. The velocity display code $CD_v$ whose value remains unchanged is supplied to the DSC 115. If the result of the determination is in the negative or if $|CD_v| \geq CD_{v(MAX)}$ is established, a calculated velocity display code $CD_v$ is equivalent to a maximum gradation level of a brightness of red or blue. In this case, the value of the velocity display code $CD_v$ is forcibly set to that of a blank code at step 308. The velocity display code $CD_v$ having undergone blanking is supplied to the DSC 115 at step 309. As a result, for example, when the $\pm CD_{v(MAx)}$ values are ±128, as far as a velocity display code $CD_v$ has a value ranging between ±127, blanking is disabled. When the velocity display code $CD_v$ has a value ranging between ±128, blanking is enabled. This characteristic is, as shown in FIG. 24, plotted as a line that falls from points indicating velocity display codes $\pm CD_{v(MAX)}$ equivalent to maximum gradation levels to a point indicating a velocity display code $CD_v$ having a value 0.

The CPU 1140 then executes the processing of steps 310 to 312 in the same manner as steps 211 to 21 3 in FIG. 12.

Owing to the aforesaid blanking, any of velocity conversion scales a to c for enhancement of a low-velocity band of tissue motion signals can be selected freely. Pixels rendering velocities that exceed a velocity threshold value $V_{th}$ determined concurrently with a velocity conversion scale a (b, or c) are blanked automatically, and a background image appears in place of the pixels.

As mentioned above, this embodiment can enjoy the advantages of the aforesaid low-velocity band enhancement and blanking. This embodiment also has the advantage that an examining physician should enter the scale conversion factor K alone using the input unit 122.

Thresholds for blanking is set to maximum gradation levels equivalent to codes $\pm CD_{v(MAX)}$. Alternatively, the thresholds may be set to codes having a lower value than the codes $\pm CD_{v(MAX)}$, if necessary. Even in this case, velocity thresholds are automatically determined concurrently with the codes. Only color pixels rendering velocities exceeding the velocity thresholds are blanked.

Fifth Embodiment

The fifth embodiment of the present invention will be described in conjunction with FIGS. 25 and 26.

Figure 25:
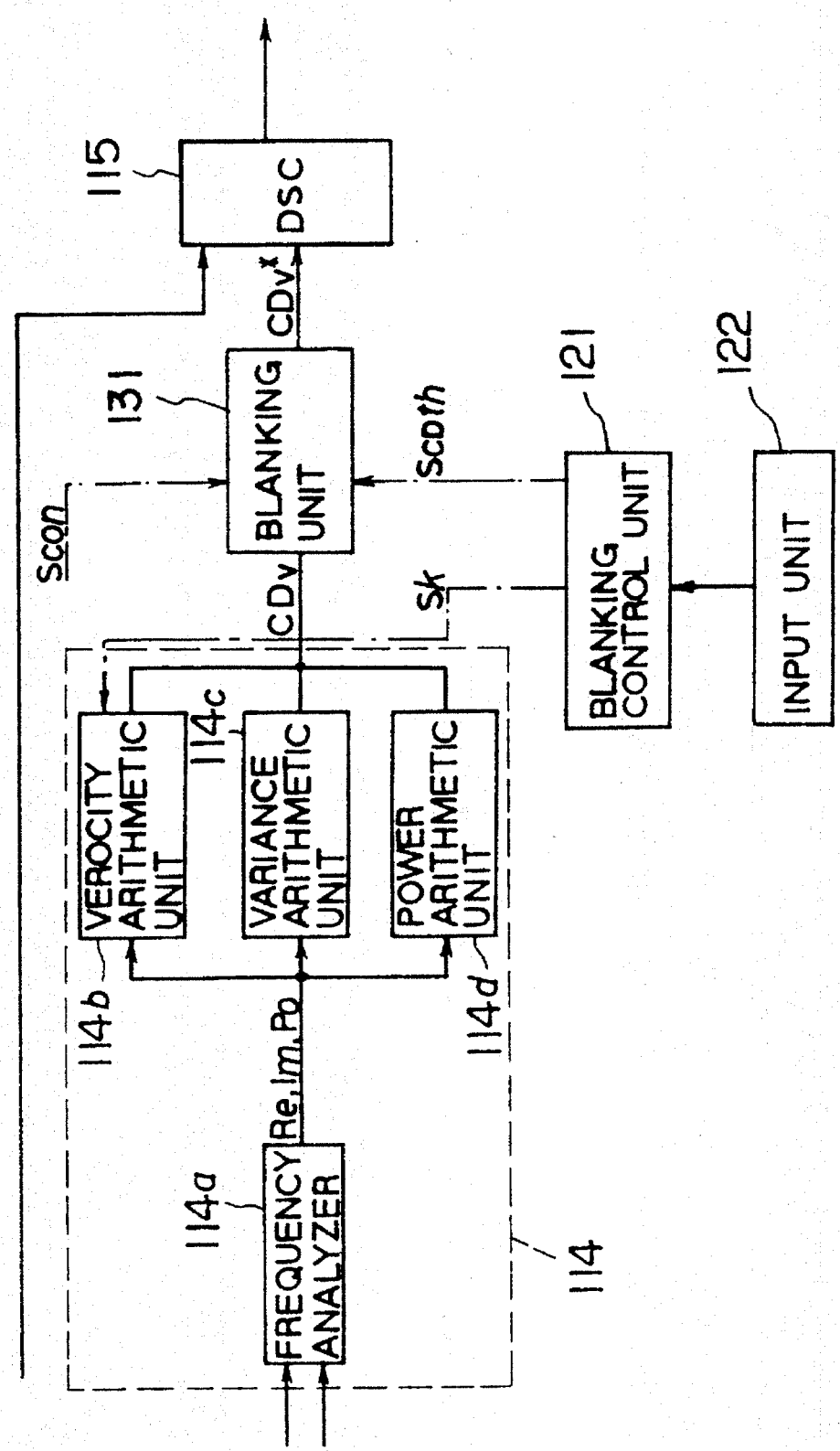
FIG. 25 is a partial block diagram showing a diagnostic ultrasound system in accordance with the fifth embodiment of the present invention.

In this embodiment, as shown in FIG. 25, a discrete blanking unit 131 is interposed between the tissue motion analyzer 114 and DSC 115 similarly to that in FIG. 16. A CPU (not shown) incorporated in the blanking unit 1 31 executes the sequence including steps shown in FIG. 26. The blanking control unit 1 21 sends the threshold signal $SCD_{th}$ representing a code threshold value $CD_{th}$ to the blanking unit 131.

Figure 26:
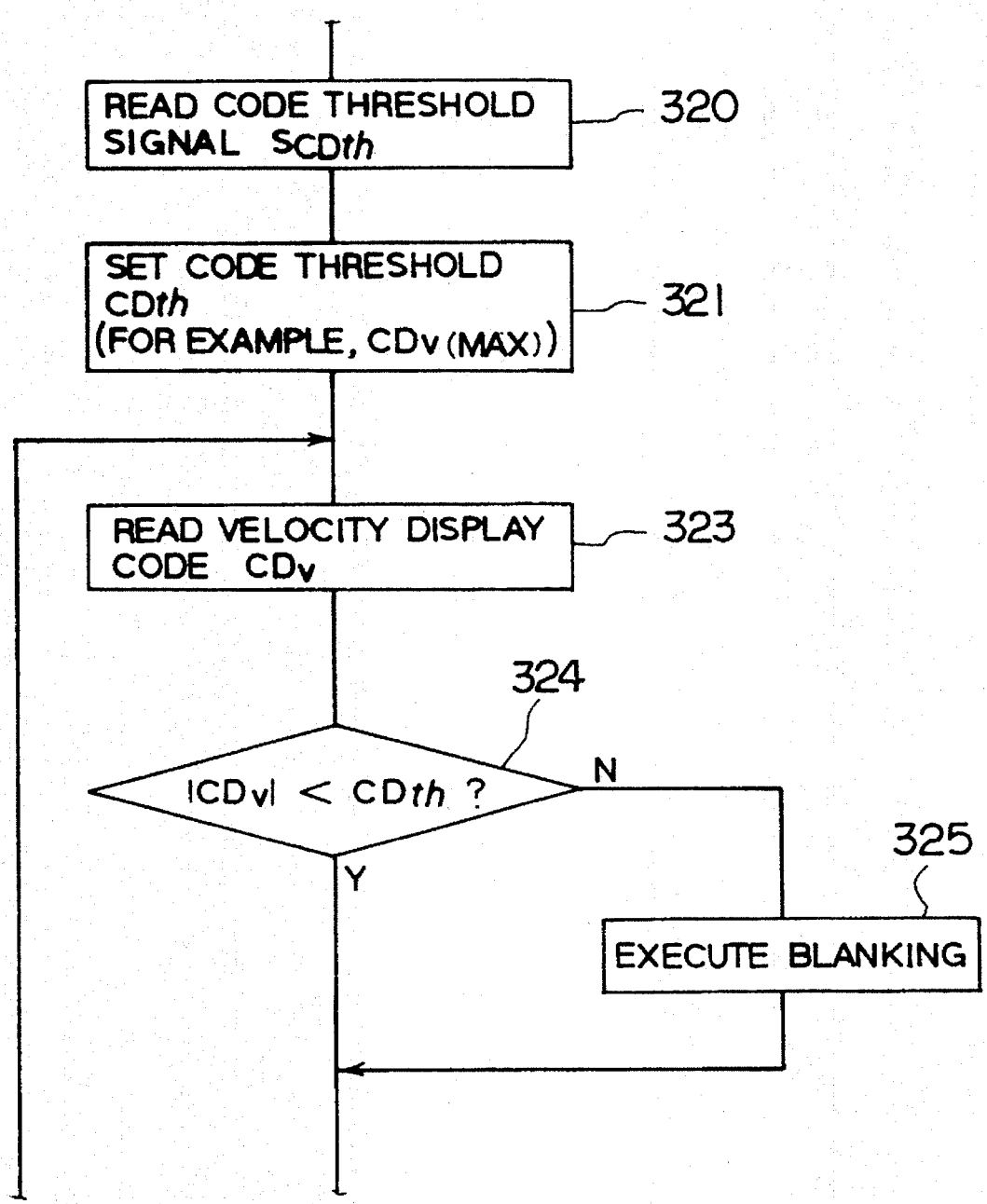
FIG. 26 is a flowchart partly describing an example of a sequence executed by a blanking control unit in the fifth embodiment.
Figure 27:
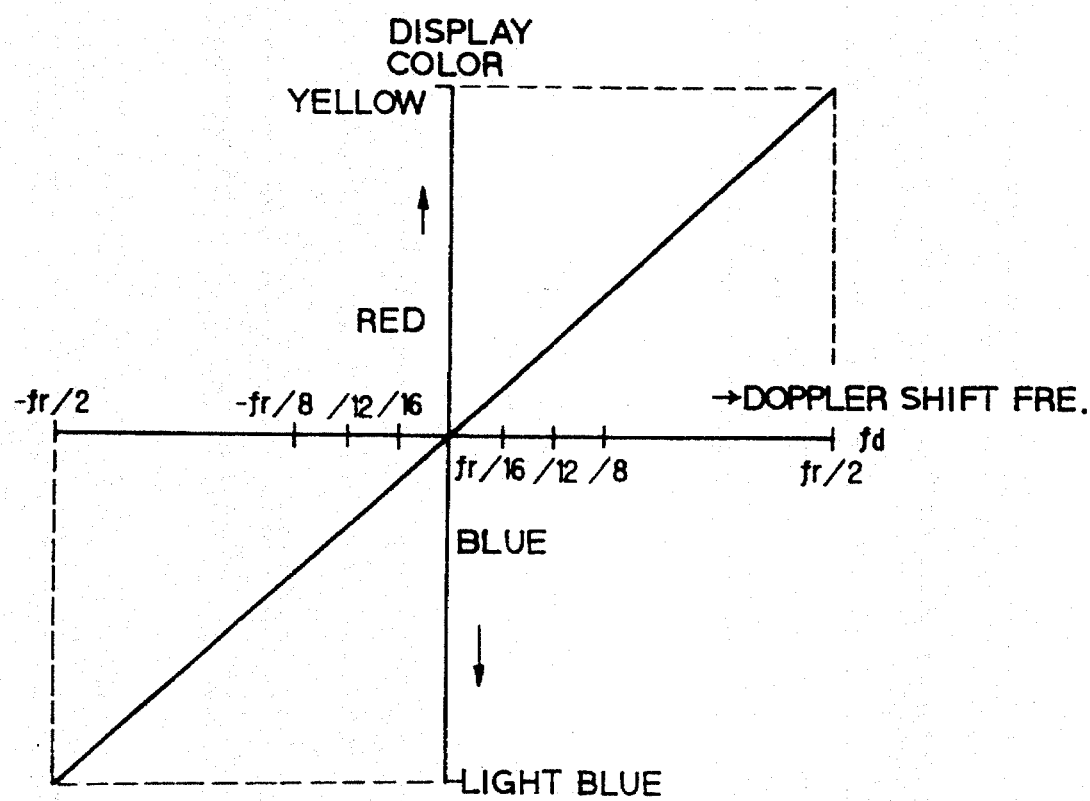
FIG. 27 shows a velocity conversion scale for blood flow velocity analysis in accordance with a prior art.

The blanking unit 131 reads the code threshold signal $SCD_{th}$ as shown in FIG. 26 and sets code thresholds $CD_{th}$ (similarly to those in the previous embodiment, $\pm CD_{v(MAx)}$) (steps 320 and 321). Thereafter, a computed velocity display code $CD_v$ is read, and it is determined whether $|CD_v|<CD_{th}$ is established (steps 323 and 324). When $|CD_v|=CD_{th}$ is established, blanking is enabled (step 325).

When a velocity range enabling blanking is to be specified at the same time of production of a velocity conversion scale, even after a velocity display code representing a velocity dependent on an average Doppler shift has been computed, the velocity range can be specified merely by setting code thresholds appropriately. Thus, the procedure is simple. Nevertheless, the same effect as that described in conjunction with FIG. 24 can be exerted.

In this embodiment, the code thresholds $S_{CDth}$ may be computed by the velocity arithmetic unit 114b and then fed to the blanking unit 131.

The DSC 115 belonging to the display system may have the capability of the aforesaid blanking unit 131 (See FIG. 21. In this case, the control signal $S_{un}$ indicating whether thresholds can be set or not need not be issued.)

In the aforesaid second to fifth embodiments and their variants, the velocity display codes $CD_v$ are expressed as gradation levels of brightnesses (luminances) of red and blue used to distinguish between tissue motion directions. Alternatively, the velocity display codes $CD_v$ may be expressed as gradation levels of hues.

For the sake of completeness it should be mentioned that the embodiment examples shown above are not definitive lists of possible embodiments. The expert will appreciate that it is possible to combine the various construction details or to supplement or modify them by measures known from the prior art without departing from the basic inventive principles.

What is claimed is:

1. A diagnostic ultrasound system for displaying a color image of a motion of a tissue contained on a subject's tomographic plane, comprising:

means for scanning an ultrasonic pulse signal along the tomographic plane so as to acquire an electrical echo signal corresponding to an ultrasonic signal reflected from the tomographic plane;

means for extracting a Doppler signal from the echo signal, said Doppler signal being Doppler-shifted by the motion of the tissue;

means for calculating velocity data concerning the motion of the tissue for respective sample points on the tomographic plane on the basis of the Doppler signal;

means for setting a scale along which each of the velocity data over a measurable band of frequencies of the Doppler signal is assigned to each gradation data for color display, said measurable band of frequencies being limited by a pulse repetition frequency of the ultrasonic pulse signal and a given low-velocity band of the measurable frequency band being enhanced in the gradation data than a remaining velocity band of the measurable band;

means for converting the velocity data into the gradation data according to the scale; and means for displaying the color image using the gradation data provided by the velocity converting means.

2. The diagnostic ultrasound system according to claim 1, wherein said extracting means comprises a low-pass filter for selectively extracting the Doppler signal.

3. The diagnostic ultrasound system according to claim 2, wherein said scale is non-linear in a ratio between changes in the velocity data and changes in the gradation data.

4. The diagnostic ultrasound system according to claim 3, wherein said ratio in the given low-velocity band is higher than said ratio in the remaining velocity band.

5. The diagnostic ultrasound system according to claim 4, wherein said specified low-velocity band is any of $-fr/8 \leq fd \leq fr/8$, $-fr/12 \leq fd \leq fr/12$, and $-fr/16 \leq fd \leq fr/16$, where fr represents the pulse repetition frequency of the ultrasonic pulse signal and fd represents a Doppler shift frequency.

6. The diagnostic ultrasound system according to claim 4, wherein said specified low-velocity band is assigned to all of the gradation data and said remaining velocity band is assigned to maximum values of the gradation data.

7. The diagnostic ultrasound system according to claim 6, wherein said ratio for said specified low-velocity band is linearly changed.

8. The diagnostic ultrasound system according to claim 6, wherein a scale portion of said scale in the specified low-velocity band is changed in a bent line divided into two line segments, one of said two line segments having higher in the ratio being assigned to a lower side on a axis representing the velocity data.

9. The diagnostic ultrasound system according to claim 1, wherein said gradation data consist of a plurality of color code data representing changes in either one of color brightness and hue, said changes expressing degrees of the velocity data in each direction of the motion of the tissue to the ultrasonic pulse signal.

10. The diagnostic ultrasound system according to claim 9, wherein at least maximum data of said color code data is discontinuous in gradation levels from a series of remaining data of said color code data.

11. The diagnostic ultrasound system according to claim 10, wherein said extracting means comprises a low-pass filter for selectively extracting the Doppler signal.

12. The diagnostic ultrasound system according to claim 11, wherein said scale is non-linear in a ratio between changes in the velocity data and changes in the gradation data.

13. The diagnostic ultrasound system according to claim 12, wherein said ratio in the given low-velocity band is higher than said ratio in the remaining velocity band.

14. A diagnostic ultrasound system for displaying a color image of a motion of a tissue contained on a subject's tomographic plane, said color image being superposed on a B-mode tomographic image of the subject's tomographic plane, said system comprising:

means for scanning an ultrasonic pulse signal along the tomographic plane to acquire an electrical echo signal corresponding to a reflected ultrasonic signal from the tomographic plane;

means for extracting a Doppler signal from the echo signal, said Doppler signal being Doppler-shifted by the motion of the tissue;

means for calculating velocity data concerning the motion of the tissue for respective sample points on the tomographic plane on the basis of the Doppler signal;

means for forming data of the B-mode tomographic image on the basis of the echo signal;

means for blanking the velocity data at every sample point when each of the velocity data exceeds a specified threshold; and means for displaying the color image by coloring the velocity data and by superimposing the velocity data subjected to blanking by the blanking means on the data of the B-mode tomographic image.

15. A diagnostic ultrasound system for displaying a color image of a motion of a tissue contained on a subject's tomographic plane, said color image being superposed on a B-mode tomographic image of the subject's tomographic plane, said system comprising:

means for scanning an ultrasonic pulse signal along the tomographic plane to acquire an electrical echo signal corresponding to a reflected ultrasonic signal from the tomographic plane;

means for extracting a Doppler signal from the echo signal, said Doppler signal being Doppler-shifted by the motion of the tissue;

means for calculating velocity data concerning the motion of the tissue for respective sample points on the tomographic plane on the basis of the Doppler signal;

means for forming data of the B-mode tomographic image on the basis of the echo signal;

means for setting a scale along which each of the velocity data over a measurable band of frequencies of the Doppler signal is assigned to each gradation data for color display, said measurable band of frequencies being limited by a pulse repetition frequency of the ultrasonic pulse signal and a given low-velocity band of the measurable frequency band being enhanced in the gradation data than a remaining velocity band of the measurable band;

means for converting the velocity data into the gradation data according to the scale;

means for blanking either one of the converted gradation data and the calculated velocity data at every sample point when each of said either one exceeds a specified threshold; and means for displaying the color image by coloring the velocity data and by superimposing the velocity data subjected to blanking by the blanking means on the data of the B-mode tomographic image.

16. The diagnostic ultrasound system according to claim 15, wherein said scale setting means is a means that sets the scale in which a ratio of changes in the gradation data to changes in the Doppler frequency is higher than a corresponding ratio for analysis of fluid motion within the subject and the velocity data larger than a reference velocity data corresponding to maximums of the gradation data are all assigned to the maximums.

17. The diagnostic ultrasound system according to claim 16, wherein said gradation data consists of a plurality of code data representing brightnesses of a specified color for every direction of the motion of the tissue to the ultrasonic pulse signal.

18. The diagnostic ultrasound system according to claim 16, wherein said gradation data consists of a plurality of code data representing hues of a specified color for every direction of the motion of the tissue to the ultrasonic pulse signal.

19. The diagnostic ultrasound system according to claim 16, further comprising means for setting the threshold independently of the scale.

20. The diagnostic ultrasound system according to claim 19, wherein said either one is the velocity data calculated by the velocity calculating means.

21. The diagnostic ultrasound system according to claim 20, wherein said velocity data calculating means comprises means for analyzing frequency components of the Doppler signal, means for computing the velocity data at each of the sample points on the basis of results analyzed by the analyzing means and wherein said velocity data computing means, said velocity data converting means and said data blanking means are incorporated into a single unit.

22. The diagnostic ultrasound system according to claim 20, wherein said specified threshold consists of values of the velocity data, said values corresponding to maximums of the gradation data defined by the scale.

23. The diagnostic ultrasound system according to claim 19, wherein said either one is the gradation data converted by the velocity data converting means and wherein said threshold setting means includes a member for setting a gradation data threshold lower than maximums of the gradation data.

24. The diagnostic ultrasound system according to claim 23, wherein said data blanking means is incorporated into an independent unit of at least the velocity data calculating means and the color image displaying means.

25. The diagnostic ultrasound system according to claim 23, wherein said color image displaying means has a digital scan converter for superimposing the velocity data on the data of the B-mode tomographic image pixel by pixel, said digital scan converter including the data blanking means.

26. The diagnostic ultrasound system according to claim 16, wherein said scale setting means is a means that automatically sets the threshold in connection with setting the scale.

27. The diagnostic ultrasound system according to claim 26, wherein said either one is the gradation data converted by the velocity data converting means.

* * * * *

UNITED STATES PATENT AND TRADEMARK OFFICE
CERTIFICATE OF CORRECTION

PATENT NO. : 5,513,640
DATED : May 07, 1996
INVENTOR(S) : Nobuo YAMAZAKI et al.

It is certified that error appears in the above-indentified patent and that said Letters Patent is hereby corrected as shown below:

In the Title, number [54] on the title page,
"ULRASOUND" should read --ULTRASOUND--.

Column 1, line 1, in the title,
"ULRASOUND" should read --ULTRASOUND--.

Signed and Sealed this

Seventeenth Day of March, 1998

Attest:

BRUCE LEHMAN

Attesting Officer

Commissioner of Patents and Trademarks